US009671925B2

(12) United States Patent
Tsukijishin et al.

(10) Patent No.: US 9,671,925 B2
(45) Date of Patent: Jun. 6, 2017

(54) IMAGE DISPLAY DEVICE AND MEDICAL IMAGE CAPTURING DEVICE

(71) Applicant: Hitachi, Ltd., Tokyo (JP)

(72) Inventors: Kenta Tsukijishin, Tokyo (JP); Kouhei Motoki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 310 days.

(21) Appl. No.: 14/419,259

(22) PCT Filed: Jul. 11, 2013

(86) PCT No.: PCT/JP2013/069051
§ 371 (c)(1),
(2) Date: Feb. 3, 2015

(87) PCT Pub. No.: WO2014/034294
PCT Pub. Date: Mar. 6, 2014

(65) Prior Publication Data
US 2015/0220240 A1    Aug. 6, 2015

(30) Foreign Application Priority Data

Aug. 28, 2012 (JP) ................................. 2012-187966

(51) Int. Cl.
*G06F 3/0481* (2013.01)
*A61B 5/00* (2006.01)
(Continued)

(52) U.S. Cl.
CPC ........ *G06F 3/04812* (2013.01); *A61B 5/7445* (2013.01); *A61B 90/37* (2016.02);
(Continued)

(58) Field of Classification Search
CPC .. G06F 3/04812; G06F 3/0482; G06F 19/321; G06F 3/04847; G06F 19/3406;
(Continued)

(56) References Cited

U.S. PATENT DOCUMENTS

2002/0048394 A1* 4/2002 Nagata ...................... G06T 7/60
382/132
2003/0183748 A1* 10/2003 Yamaguchi ............ H04N 17/04
250/208.1
(Continued)

FOREIGN PATENT DOCUMENTS

JP          11-102007 A       4/1999
JP          2004-283372       10/2004
(Continued)

OTHER PUBLICATIONS

International Preliminary Report on Patentability received in corresponding International Application No. PCT/JP2013/069051 dated Mar. 12, 2015.
(Continued)

*Primary Examiner* — Sath V Perungavoor
*Assistant Examiner* — Howard D Brown, Jr.
(74) *Attorney, Agent, or Firm* — Mattingly & Malur, PC

(57) ABSTRACT

An object of the present invention is to display measurement result with maintaining good visibility for a peripheral part of measurement area. The image display device of the present invention comprises a cursor processing part that performs control for generating an area cursor 81 that indicates a measurement area on a medical image, an identification label 83 including identification information for specifically identifying the area cursor 81, and a result label 82 including the identification information and a measurement result, and displaying them on a screen, and an operation part that receives an operation of setting the area cursor and moving the result label. When the area cursor 81 is set, the result label 82 is attached to the area cursor 81, and they are displayed. Then, an operation for moving the result label 82 is performed, the result label 82 is separated from the area cursor 81, and made movable, an identification label (Continued)

83 is attached to the area cursor 81 instead of the result label 82, and they are displayed.

17 Claims, 17 Drawing Sheets

(51) Int. Cl.
| | |
|---|---|
| *G06F 19/00* | (2011.01) |
| *G06F 3/0482* | (2013.01) |
| *G06F 3/0484* | (2013.01) |
| *G06T 7/00* | (2017.01) |
| *A61B 90/00* | (2016.01) |
| *A61B 19/00* | (2006.01) |
| *A61B 8/08* | (2006.01) |

(52) U.S. Cl.
CPC ........ *G06F 3/0482* (2013.01); *G06F 3/04847* (2013.01); *G06F 19/321* (2013.01); *G06F 19/3406* (2013.01); *G06T 7/0012* (2013.01); *A61B 8/0858* (2013.01); *A61B 2090/374* (2016.02); *A61B 2090/378* (2016.02); *A61B 2090/3762* (2016.02); *G06T 2207/10072* (2013.01); *G06T 2207/30004* (2013.01)

(58) Field of Classification Search
CPC .................. A61B 90/37; A61B 5/7445; A61B 2090/3762; A61B 2090/378; A61B 2090/374; G06T 7/0012; G06T 2207/30004; G06T 2207/10072
See application file for complete search history.

(56) References Cited

U.S. PATENT DOCUMENTS

| | | | | |
|---|---|---|---|---|
| 2004/0207661 | A1* | 10/2004 | Akaki | A61B 5/416 715/764 |
| 2006/0274145 | A1* | 12/2006 | Reiner | G06F 17/3028 348/62 |
| 2007/0274586 | A1* | 11/2007 | Yamano | G09G 5/02 382/162 |
| 2008/0228061 | A1* | 9/2008 | Habets | G06T 7/62 600/407 |
| 2011/0002522 | A1* | 1/2011 | Goto | G06T 7/0012 382/131 |
| 2012/0078396 | A1* | 3/2012 | Case, Jr. | A63B 24/00 700/91 |
| 2013/0214141 | A1* | 8/2013 | Hogo | G01D 11/24 250/234 |

FOREIGN PATENT DOCUMENTS

| | | |
|---|---|---|
| JP | 2007-521864 A | 8/2007 |
| JP | 2012-95691 A | 5/2012 |

OTHER PUBLICATIONS

International Search Report in PCT/JP2013/069051, dated Aug. 6, 2013.

\* cited by examiner

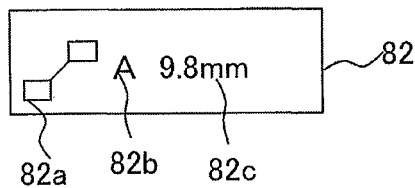
(a)
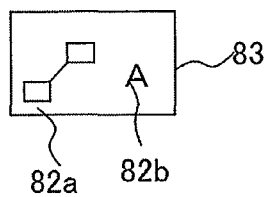
(b)
Fig. 4
| Medical image number | Type | Starting point | End point | Identification name | Measurement result | Time stamp |
|---|---|---|---|---|---|---|
| Medical image 70 | Distance | (x1, y1) | (x2, y2) | A | 9.8mm | t1 |
| Medical image 70 | Distance | (x3, y3) | (x4, y4) | B | 9.4mm | t2 |
| Medical image 70 | Distance | (x5, y5) | (x6, y6) | C | 9.9mm | t3 |
| Medical image 130 | Angle | (x7, y7) | (x8, y8) | A |  | t4 |
| Medical image 130 | Angle | (x9, y9) | (x10, y10) | B | 25° | t5 |
| Medical image 140 | Area | (x11, y11) | (x12, y12) | A | 5cm² | t6 |
Fig. 5      90

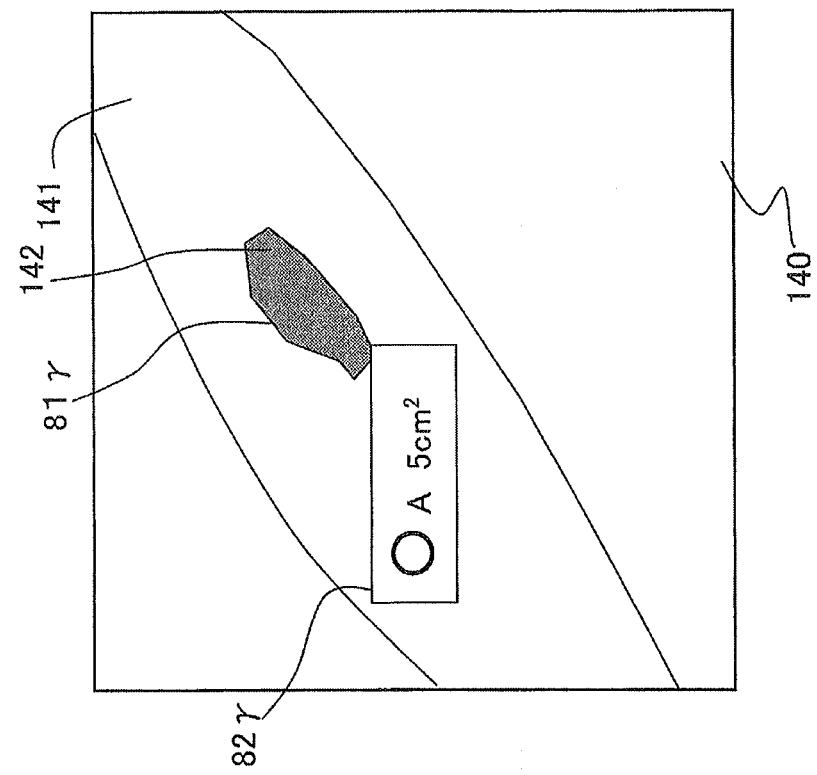
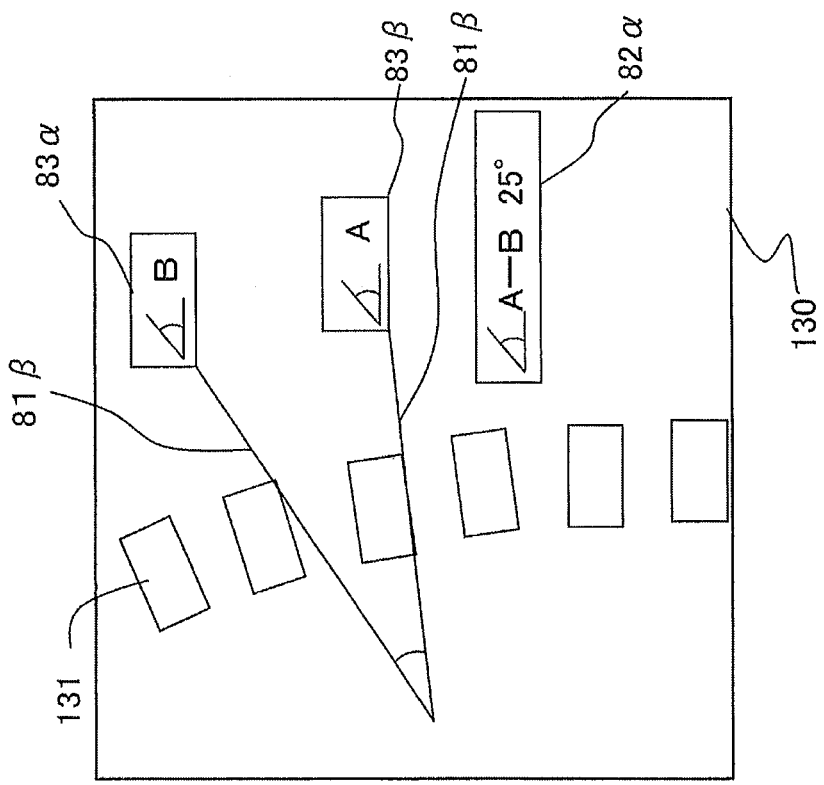
Fig. 9

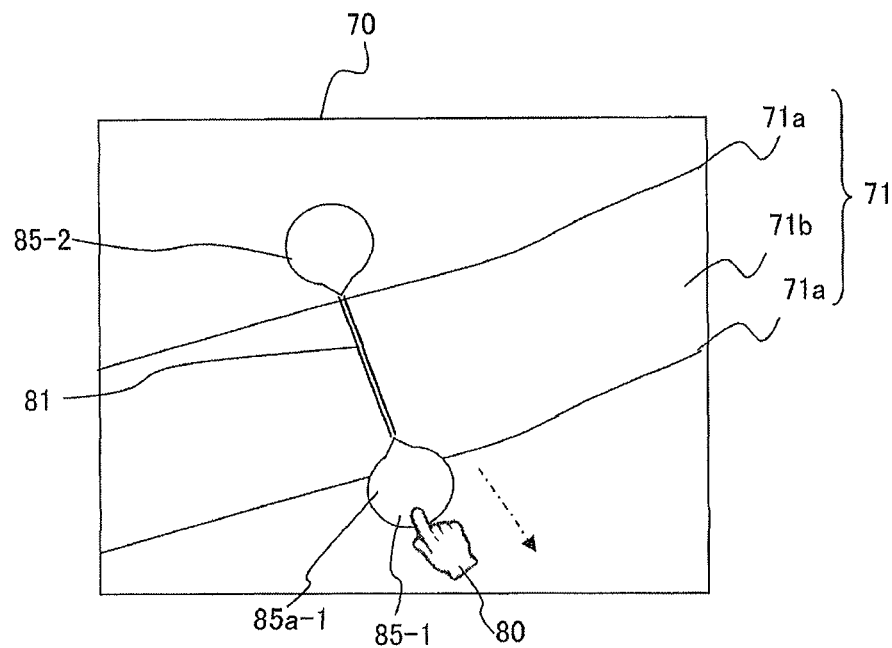
(a)
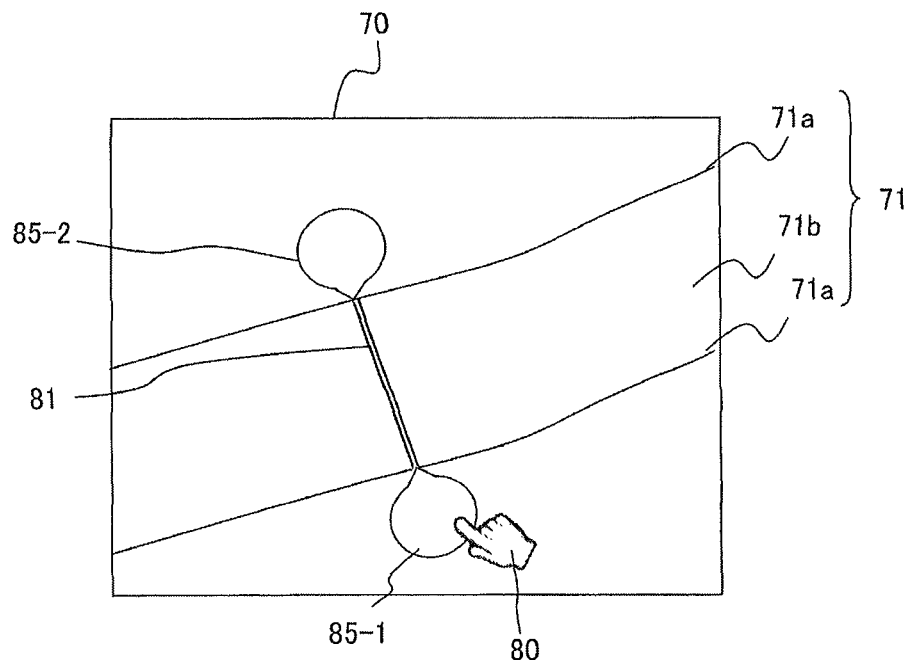
(b)
Fig. 13

IMAGE DISPLAY DEVICE AND MEDICAL IMAGE CAPTURING DEVICE

TECHNICAL FIELD

The present invention relates to an image display device and a medical image-capturing device, especially, a technique for measurement on a medical image.

BACKGROUND ART

Patent document 1 discloses an analytical processing unit for setting two points on a medical image, and measuring a distance between the two points in the direction along the central line thereof.

PRIOR ART REFERENCES

Patent Document

Patent document 1: Japanese Patent Unexamined Publication (KOKAI) No. 2004-283372

SUMMARY OF THE INVENTION

Object to be Achieved by the Invention

Measurement of a distance on a medical image suffers from a problem that if the display position of the measurement result is unduly remote from measurement area, it becomes difficult to confirm the measurement result, whereas if the display of the measurement result overlaps with the measurement area, visibility is degraded for a part around the measurement area.

An object of the present invention is to display measurement result with maintaining good visibility for a part around the measurement area.

Means for Achieving the Object

In order to achieve the aforementioned object, the image display device of the present invention comprises a first operation part that receives an operation of specifying a measurement area on a medical image displayed on a screen of a display device, a measurement part that measures a physical quantity of the measurement area, a cursor processing part that performs control for generating an area cursor that indicates the measurement area, an identification label including identification information for specifically identifying the area cursor, and a result label including the identification information and a measurement result obtained by the measurement part, and displaying them on the screen, and a second operation part that receives an operation of moving the result label, wherein when the first operation part receives specification of the measurement area, the cursor processing part displays the area cursor, when the measurement performed by the measurement part is completed, the cursor processing part attaches the result label to one end point of the area cursor and displays them, and when the second operation part receives an operation of moving the result label, the cursor processing part separates the result label from the area cursor and displays it following the moving operation, and displays the identification label at the one end point of the area cursor at which the result label has been attached.

Effect of the Invention

According to the present invention, a measurement result can be displayed with maintaining good visibility of a region around a measurement area.

BRIEF DESCRIPTION OF THE DRAWINGS

FIG. 4 is an explanatory drawing showing configuration of the result label and the identification label, in which (a) is configuration of the result label and (b) is configuration of the identification label.

FIG. 5 is an explanatory drawing showing an example of contents of the area cursor information.

FIG. 9 is an explanatory drawing showing another example of the area cursor, in which (a) is an area cursor for measuring angle and (b) is an area cursor for measuring area.

FIG. 13 is an explanatory drawing showing a processing for changing position of the end point of the area cursor using the end point cursor, in which (a) is a state before the change and (b) is a state after the change.

MODES FOR CARRYING OUT THE INVENTION

The image display device according to an embodiment of the present invention comprises a first operation part that receives an operation of specifying a measurement area on a medical image displayed on a screen of a display device, a measurement part that measures a physical quantity of the measurement area, a cursor processing part that performs control for generating an area cursor that indicates the measurement area, an identification label including identification information for specifically identifying the area cursor, and a result label including the identification information and a measurement result obtained by the measurement part, and displaying them on the screen, and a second operation part that receives an operation of moving the result label, wherein when the first operation part receives specification of the measurement area, the cursor processing part displays the area cursor, when the measurement performed by the measurement part is completed, the cursor processing part attaches the result label to one end point of the area cursor and displays them, and when the second operation part receives an operation of moving the result label, the cursor processing part separates the result label from the area cursor and displays it following the moving operation, and displays the identification label at the one end point of the area cursor at which the result label has been attached.

The medical image-capturing device of the present invention comprises the aforementioned image display device, and an image-capturing part that captures an image of a subject and obtains image signals, wherein the image display device further comprises an image-generating part that generates a medical image of the subject on the basis of the image signals.

Hereafter, details of embodiments of the aforementioned image display device carried on a medical image-capturing device will be explained with reference to the drawings.

Figure 1:
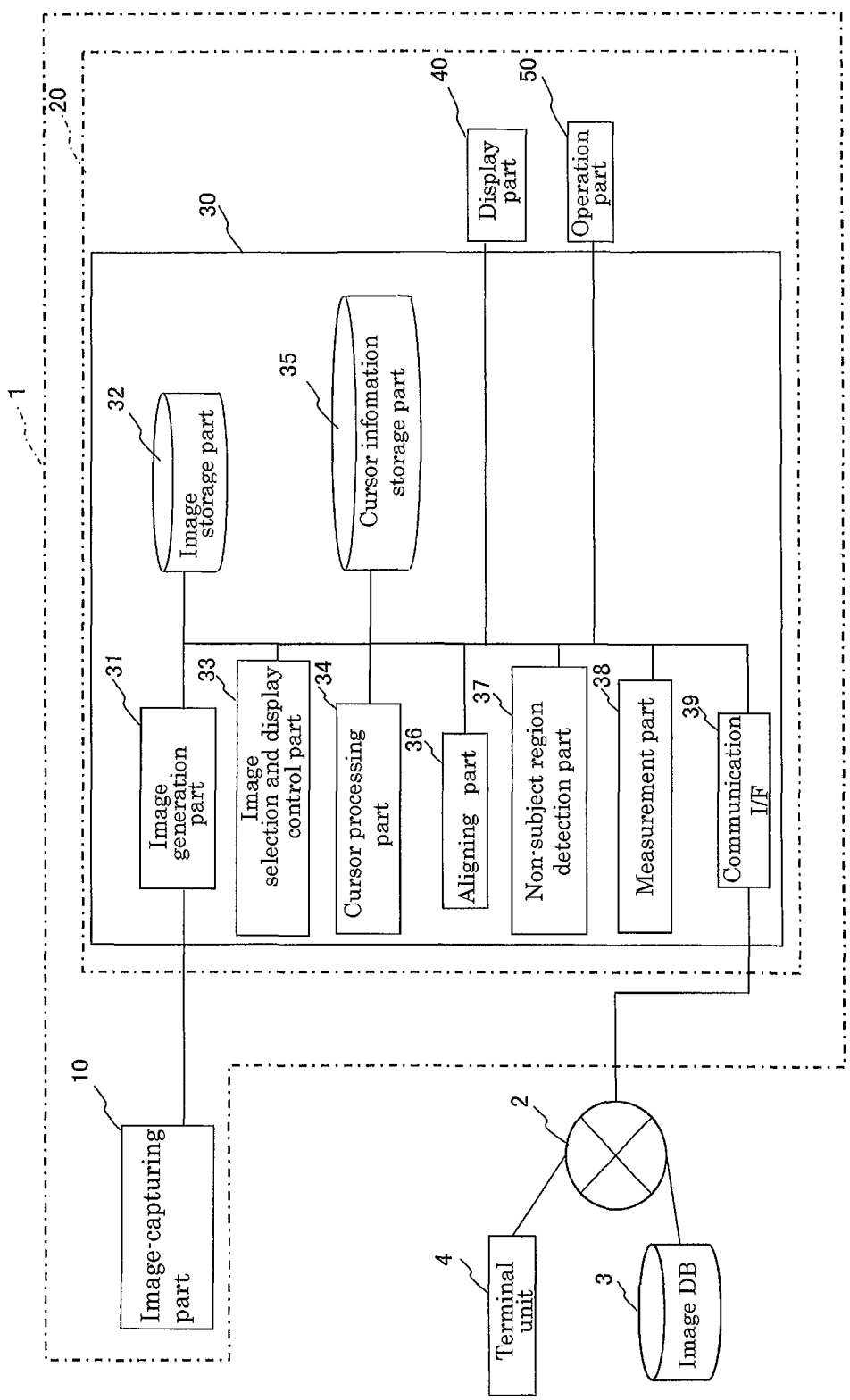
FIG. 1 is a functional block diagram of a medical image-capturing device according to an embodiment of the present invention.

FIG. 1 is a functional block diagram of a medical image-capturing device according to an embodiment of the present invention. As shown in FIG. 1, the medical image-capturing device 1 is communicably connected to an intrahospital network 2, such as LAN. Further, to the intrahospital network 2, an image database (henceforth abbreviated as "image DB"), such as a PACS (Picture Archiving and Communication Systems) server, and a terminal unit 4 that reads out a medical image from the image DB 3 and displays it are connected.

The medical image-capturing device 1 may be a medical image-capturing device comprising an image-capturing part that captures an image of a subject and generates image data, and the image display device of the present invention, and it may be a medical image-capturing device of any type, such as X-ray image diagnostic apparatus, X-ray CT scanner, MRI apparatus, ultrasonic diagnostic apparatus, and PET apparatus. The image display device of the present invention may not be carried on a medical image-capturing device, either, and may be applied to a so-called stand alone image display device, which is not connected to such a terminal unit 4 or network as mentioned above.

The medical image-capturing device 1 comprises an image-capturing part 10 that captures an image of a subject and obtains image signals, and an image display device 20 that generates a medical image of the subject on the basis of the image signals and performs measurement processing on the medical image. The image display device 20 comprises a control part 30 that controls operations concerning generation and display of a medical image, a display part 40 that displays the medical image, and an operation part 50 for an operator to input directions.

The image-capturing part 10 is for obtaining image signals of the subject, and if the medical image-capturing device is an X-ray image diagnostic apparatus, it comprises an X-ray generator that generates X-rays, an X-ray detector for detecting transmitted X-rays that have transmitted through the subject, and outputting electric signals corresponding to intensities of the transmitted X-rays, and an image-capturing part controlling apparatus that controls operations of the foregoing apparatuses. If the medical image-capturing device is an X-ray CT scanner, the image-capturing part 10 comprises a rotatable gantry carrying an X-ray tube and an X-ray detector. If the medical image-capturing device is an ultrasonic diagnostic apparatus, the image-capturing part 10 comprises a probe and ultrasonic transmission and reception part required for transmission and reception of ultrasonic waves. If the medical image-capturing device is an MRI apparatus, the image-capturing part 10 comprises a magnetic field coil, pulse sequence generator etc. required for reception of NMR signals.

The control part 30 comprises an image generation part 31 that generates a medical image of a subject or performs reconstruction processing of medical image on the basis of the image data generated by the image-capturing part 10, an image storage part 32 that stores the generated medical image, an image selection and display control part 33 that selects a medical image for display on a display part 40 and controls the display, a cursor processing part 34 that controls generation and display of an area cursor that indicates a measurement area, a result label including identification information for specifically identifying the area cursor and measurement result, an identification label including the aforementioned identification information, an end point cursor that indicates an end point of the measurement area, a vertical guiding line displayed together with the area cursor, a label box for collectively indicating result labels, and a mouse cursor, a cursor information storage part 35 that stores cursor information, an aligning part 36 that aligns and displays the result labels, a non-subject region detection part 37 that detects a region of a medical image in which a subject is not imaged (henceforth referred to as "non-subject region"), a measurement part 38 that measures a predetermined physical quantity (distance, angle, area, etc.) that characterizes a measurement area specified on the medical image, and a communication interface (henceforth referred to as "communication I/F") 39 for connection with an intrahospital network 2. The control part 30 is constituted by a combination of software for realizing the functions of the components of the control part 30 and hardware including an arithmetic operation and control unit and storage device.

The display part 40 comprises and constituted by a display memory for temporarily storing display data, and a display device comprising a liquid crystal display monitor, CRT, organic electroluminescence panel, or the like.

The operation part 50 comprises arbitrary operation devices, such as pointing device, keyboard, and software button displayed on the screen, for choosing and specifying an arbitrary coordinate on a medical image displayed on the screen of the display part 40. As the pointing device, an arbitrary device such as mouse, trackball, and touch panel laminated on or under the screen of the display device can be used.

Hereafter, embodiments of processing of specifying a measurement area on a medical image, measuring a physical quantity, and displaying a measurement result, which are mainly performed by the cursor processing part, will be explained.

First Embodiment

This embodiment is characterized as follows. That is, the cursor processing part 34 performs the following basic operations. Namely, when the operation part 50 (first operation part) receives specification of a measurement area, the cursor processing part 34 displays an area cursor, and when the measurement performed by the measurement part 38 is completed, the cursor processing part 34 attaches a result label to one end point of the area cursor and displays them. Further, when the operation part (second operation part) receives an operation of moving the result label, the cursor processing part 34 separates the result label from the area cursor and displays it following the moving operation, and displays an identification label at the one end point of the area cursor at which the result label has been attached. In addition to the above basic operations, the aligning part 36 aligns result labels having been separated from the area cursor in accordance with a predetermined alignment condition.

The cursor processing part 34 displays the aligned result labels. Alternatively, the cursor processing part 34 generates a label box accommodating a plurality of the aligned result labels, and displays it. In the latter case, when the operation part (second operation part) receives selection and moving operations of an arbitrary result label in the label box, the cursor processing part 34 may divide the label box into a plurality of divided label boxes at the selected result label as a border, move the divided label box including the selected result label, and display it following the moving operation.

When the device further comprises a non-subject region detection part that detects a non-subject region, where the subject is not imaged, in a medical image, the cursor processing part 34 may display the aligned result labels in the non-subject region.

Figure 2:
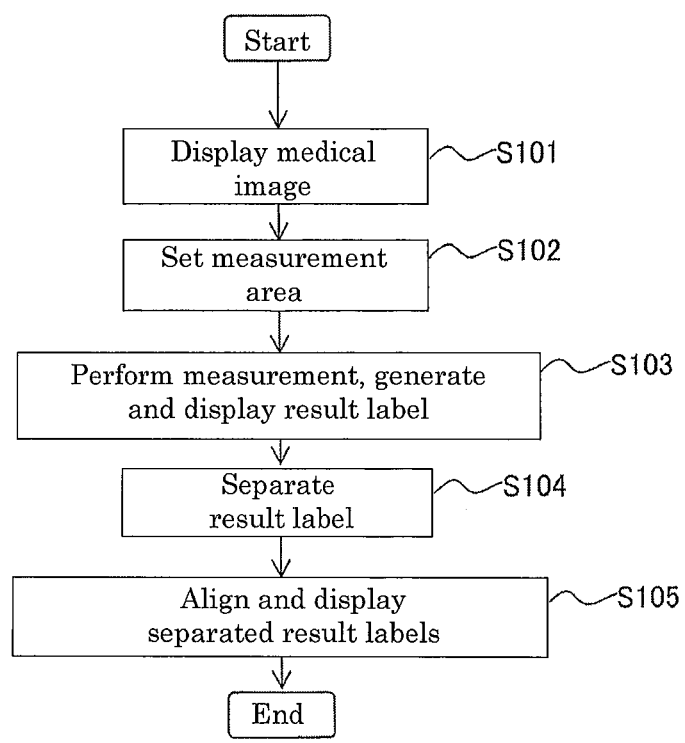
FIG. 2 is a flowchart showing flow of a processing for setting of area cursor.
Figure 3:
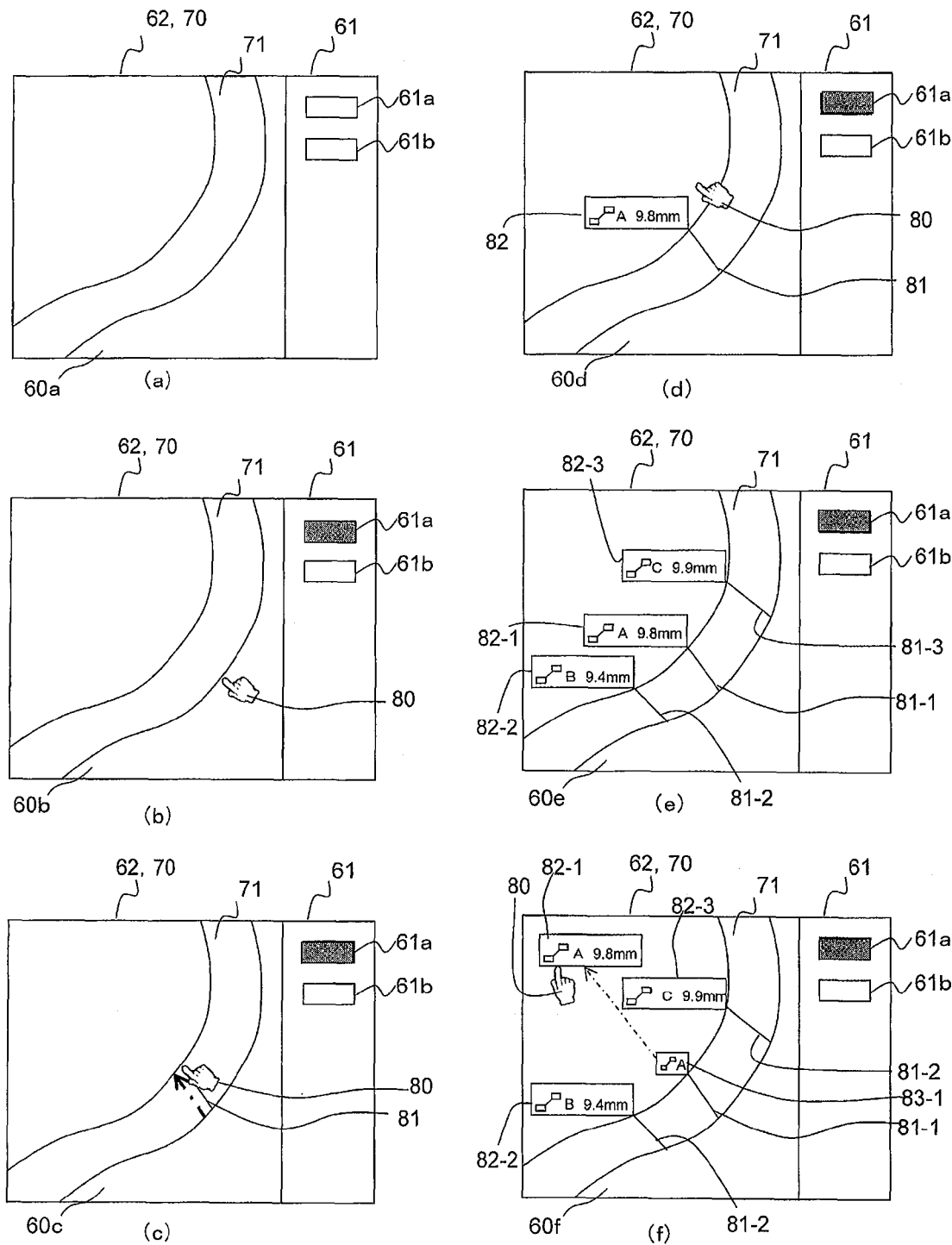
FIG. 3 is an explanatory drawing showing an example of transition of display displayed in a processing for setting of area cursor, in which (a) is an example of display displayed in Step S101, (b) is an example of display displayed in Step S102, (c) is an example of display displayed in Step S102, (d) is an example of display displayed in Step S103, (e) is an example of display displayed in Step S103, and (f) is an example of display displayed in Step S104.
Figure 6:
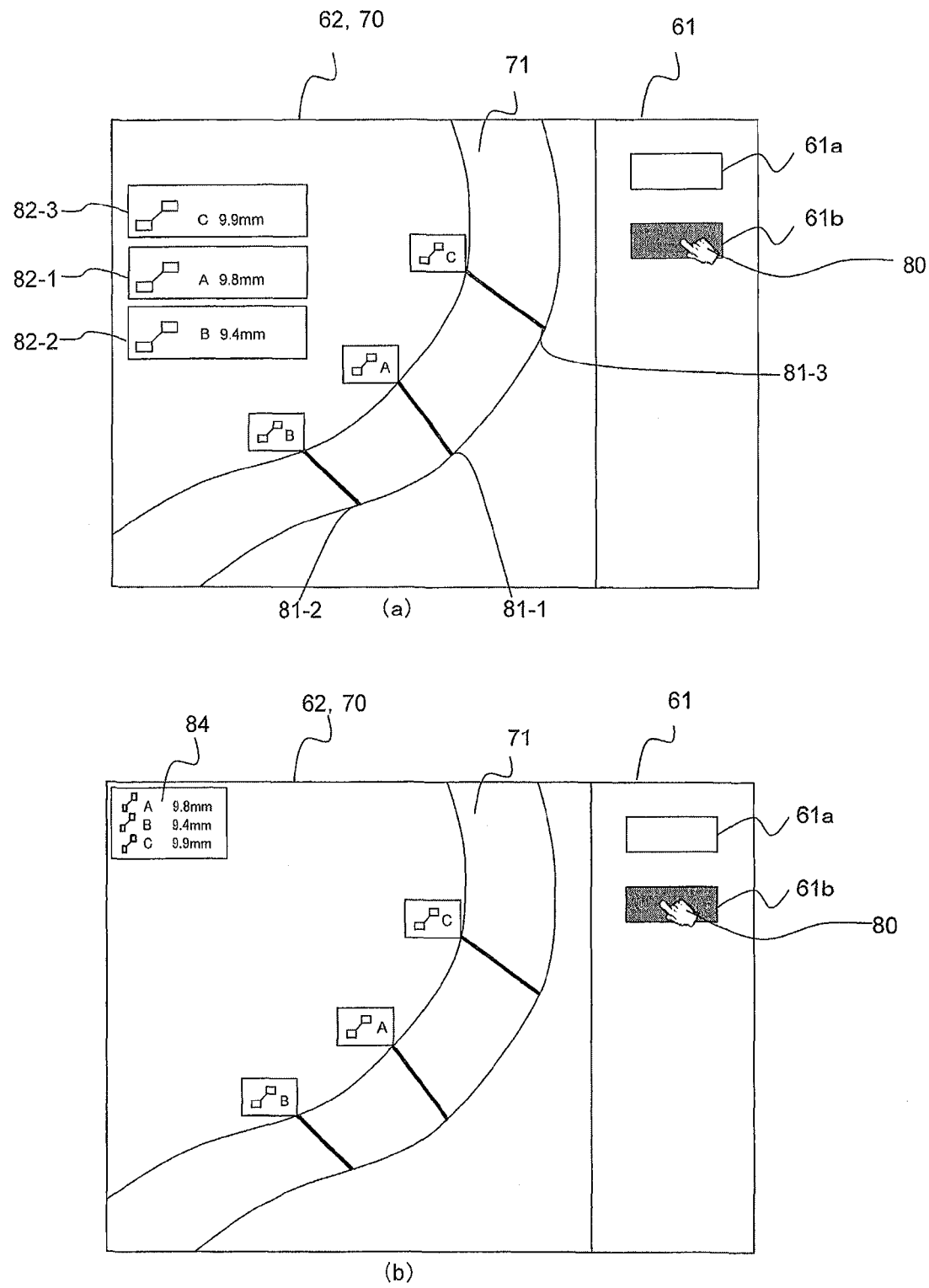
FIG. 6 is an explanatory drawing showing alignment processing of the identification label, in which (a) is an example of display of separated and aligned result labels, and (b) is an example of display of aligned result labels displayed by using a label box.
Figure 7:
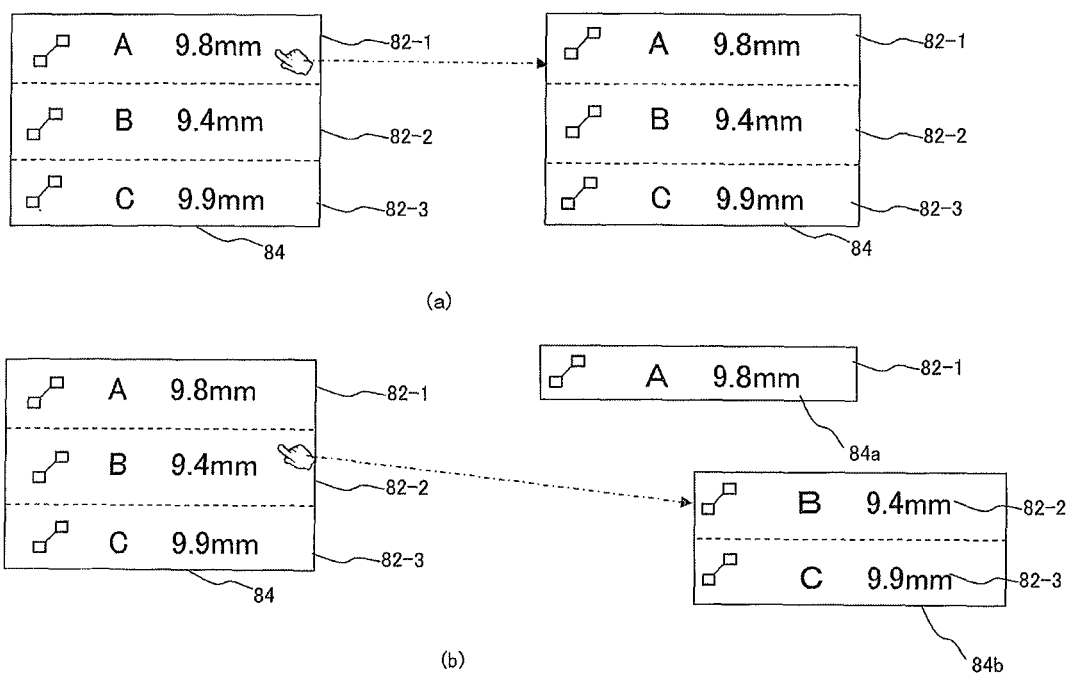
FIG. 7 is an explanatory drawing showing separation processing of label box, in which (a) is a state that the uppermost result label is specified, and (b) is a state that the second result label from the top is specified.
Figure 8:
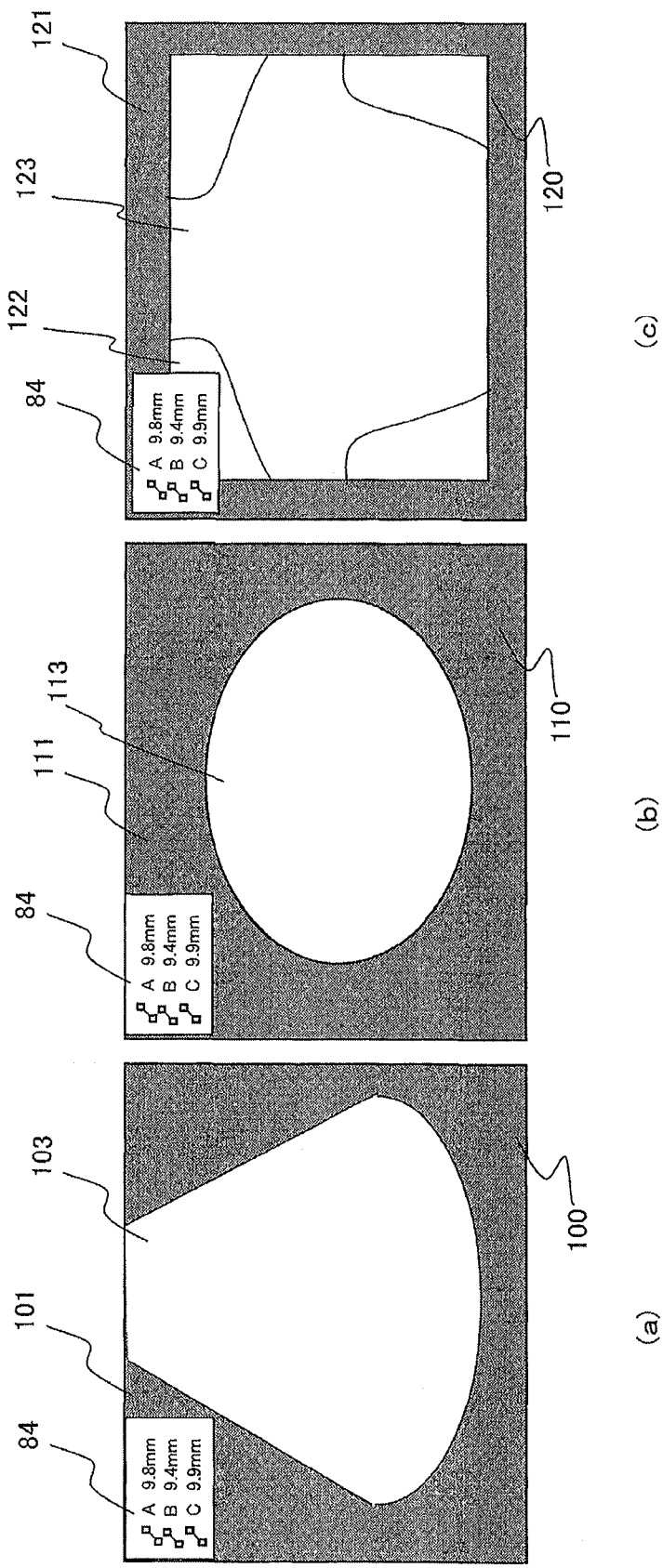
FIG. 8 is an explanatory drawing showing a non-subject region in a medical image, in which (a) is a non-field-of-view region of an ultrasonogram, (b) is an air region of an X-ray CT image, and (c) is an X-ray shutter region of an X-ray image.

Hereafter, this embodiment will be explained in detail with reference to FIGS. 2 to 9. FIG. 2 is a flowchart showing the flow of the processing concerning setting of the area cursor. FIG. 3 includes explanatory drawings showing examples of transition of display displayed in the processing for setting of the area cursor. In FIG. 3, (*a*) shows an example of display displayed in Step S101, (*b*) shows an example of display displayed in Step S102, (*c*) shows an example of display displayed in Step S102, (*d*) shows an example of display displayed in Step S103, (*e*) shows an example of display displayed in Step S103, and (*f*) shows an example of display displayed in Step S104. FIG. 4 includes explanatory drawings showing configurations of the result label and identification label, and in FIGS. 4, (*a*) and (*b*) show the configuration of the result label and the configuration of the identification label, respectively. FIG. 5 is an explanatory drawing showing an example of contents of the area cursor information. FIG. 6 includes explanatory drawings showing alignment processing of the identification label, and n FIGS. 6 (*a*) and (*b*) show examples of display of separated and aligned result labels, and display of result labels using a label box, respectively. FIG. 7 includes explanatory drawings showing separation processing of a label box, and in FIGS. 7 (*a*) and (*b*) show a state that the uppermost result label is specified, and a state that the second result label from the top is specified, respectively. FIG. 8 includes explanatory drawings showing a non-subject region, and in FIG. 8 (*a*) to (*c*) show a non-field-of-view region of an ultrasonogram, air region of an X-ray CT image, and direct X-ray exposure region and X-ray shutter region of an X-ray image, respectively. FIG. 9 includes explanatory drawings showing other examples of the area cursor, and in FIGS. 9 (*a*) and (*b*) show an area cursor for measuring angle and an area cursor for measuring area, respectively.

Hereafter, explanations will be made in accordance with the order of the steps shown in FIG. 2. Before the start of the measurement processing shown in FIG. 2, an image of a subject is captured by the image-capturing part 10, and image signals are obtained. The image generation part 31 generates or reconstructs a medical image by using the image signals. The generated medical image is stored in the image storage part 32. Then, Step S101 is started.

(Step S101)

The image selection and display control part 33 reads out a medical image to be displayed from the image storage part 32, or obtains a medical image to be displayed from the image DB 3 via the communication I/F 39, and displays it on the screen of the display part 40 (S101). FIG. 3 (*a*) shows an example of display displayed in this step. A display 60*a* shown in FIG. 3 (*a*) includes a button region 61 where software buttons are displayed, and an image display region 62 where a medical image is displayed. In the display 60*a*, a medical image 70 in which image of a blood vessel 71 is captured is displayed in the image display region 62. In the button region 61, there are displayed a "Measurement" button 61*a* for inputting a direction for starting the measurement, and an "Alignment" button 61*b* for inputting a direction for aligning result labels.

(Step S102)

On the displayed medical image, a measurement area as an object for which a physical quantity is measured is set (S102). The explanations of this embodiment will be made for a processing of measuring width (distance) of the blood vessel 71 as an example.

When an operator operates the operation part 50 to move a mouse cursor 80 to the "Measurement" button 61*a* and perform an operation such as clicking a mouse button, input of a measurement area on the medical image 70 becomes possible (in FIG. 3, the colored button 61*a* indicates a pressed state of the button).

Then, the operator performs an operation of inputting one end point of the measurement area (henceforth referred to as "starting point") by using the operation part 50. This input operation is performed by, for example, moving the mouse cursor 80 to a wall of the blood vessel as the object of the measurement, and clicking a mouse button. The display 60*b* shown in FIG. 3 (*b*) displays a state that the mouse cursor 80 has been moved to the position as the starting point.

In this state, as shown in the display 60c shown in FIG. 3 (c), the mouse cursor 80 is dragged along the measurement object area to specify the whole measurement area. The alternate long and short dash line drawn in FIG. 3(c) indicates the direction of the movement. The cursor indicating the whole measurement area is called area cursor. In the display 60c, the cursor in the form of a line segment extending from the mouse cursor 80 corresponds to the area cursor 81.

Then, the operator performs an operation of inputting an end point position of the measurement area, for example, moving the cursor to the other blood vessel wall of the measurement object (symmetric position of the position inputted as the starting point) and clicking a mouse button. (Step S103)

When the end point of the measurement area is inputted, the measurement part 38 measures distance of the measurement area specified with the area cursor 81, and the cursor processing part 34 generates and displays a result label including a measurement result (S103). In this embodiment, when the operator moves the mouse cursor 80 to the end point and performs the operation of inputting the end point position (for example, clicking a mouse button), the cursor processing part 34 executes a processing of attaching the result label 82 to the end point of the area cursor 81 and displaying them, which is triggered by the above input operation. The display 60d shown in FIG. 3D displays a state that the result label 82 attached to the area cursor 81 is displayed. In addition, after the input of the end point position of the measurement area, the mouse cursor 80 can be separated from the area cursor 81, and moved to an arbitrary position on the medical image 70.

As shown in FIG. 4 (a), the result label 82 includes a classification icon 82a that indicates type of the physical quantity measured with the area cursor, i.e., distance, area, or angle, identification information 82b for specifically identifying the area cursor 81, and a result value 82c obtained as a result of the measurement.

If the processings of Step S102 and Step S103 are repeated a plurality of times for different positions of the blood vessel 71, the area cursors 81 set in the plurality of times of the measurement and the result labels 82 attached to the end points of the respective area cursors 81 are displayed. The display 60e shown in FIG. 3 (e) is an example of the display to be displayed after the measurement is performed for three different positions of the blood vessel 71, and shows three area cursors 81-1, 81-2, and 81-3, and result labels 82-1, 82-2, and 82-3 attached to the area cursors, respectively. Since the area cursor 81-1 and the result label 82-1 are the same as the area cursor 81 and the result label 82 displayed in the display 60d, respectively, they are depicted with the same identification information "A".

The cursor processing part 34 displays the result labels 82-1, 82-2, and 82-3, and stores information on the area cursors 81 in the cursor information storage part 35. As shown in FIG. 5, the area cursor information 90 includes information concerning the area cursor 81, such as information for specifying the medical image in which the area cursor 81 has been set (corresponding to "Medical image number"), classification of the area cursor 81, positional information of the area cursor (for example, coordinates of the starting point and end point), identification information of the area cursor 81 (corresponding to "Identification name"), measurement result, and time of setting of the area cursor 81 (corresponding to "Time stamp".), and is stored in the cursor information storage part 35.

Since the identification names of the area cursor 81 are independently assigned for each medical image in FIG. 5, the same identification names are used for different medical images. The coordinates of the starting point and end point of the area cursor 81 are absolute coordinates based on each medical image. If the area cursor information 90 is stored, even when display of a medical image for which the area cursor 81 has been set is ended, and the medical image is displayed again, the cursor processing part 34 can access the area cursor information 90, and display the medical image, the result labels etc. previously displayed.

Although not shown in the drawing, the cursor information storage part 35 also stores image data used for the area cursor, result label, identification label, mouse cursor, and end point cursor described later.

(Step S104)

The result label 82 is separated (S104). For example, the operator performs an operation for selecting a result label 82 as an object of the separation (for example, clicking a mouse button), and an operation for moving the result label (for example, dragging). The cursor processing part 34 separates the result label 82 from the end point of the area cursor 81, and at the same time, generates an identification label 83 including a classification icon 82a and identification information 82b, but not including a measurement result, as shown in FIG. 4(b). Then, the identification label 83 is attached to the end point of the area cursor 81, instead of the separated result label 82, and displayed. Although the display position of the identification label 83 is fixed at the end point of the area cursor 81, the separated result label 82 can be moved to an arbitrary position in the image display region 62.

The display 60f shown in FIG. 3 (f) displays a state that the result label 82-1 is dragged with the mouse cursor 80 (the moving direction is indicated with an alternate long and short dash line in FIG. 3 (f)) to separate it from the area cursor 81-1, and an identification label 83-1 attached to the end point of the area cursor 81-1 is displayed. In the display 60f, only the result label 82-1 is separated, but the other result labels 82-2 and 82-3 can also be separated and displayed in the same manner as that of the result label 82-1.

(Step S105)

The separated result labels are aligned and displayed (S105). When the operator performs an input operation for aligning the separated result labels (for example, clicking the alignment button 61b shown in FIG. 6), the aligning part 36 accesses the area cursor information 90 to refer to the predetermined alignment conditions set in the aligning part 36 beforehand, and aligns the result labels 82 separated from the area cursors 81 according to the alignment conditions, and the cursor processing part 34 displays the aligned result labels 82. Examples of the alignment conditions include "order of time series", which corresponds to order of impartation time of the result label 82, "order of identification name" (for example, alphabetical order, when the name consists of alphabets), "order of result value", which is ascending order or descending order of the result value, "disposition order" (order of coordinate) of the result label 82, and so forth.

In this embodiment, when the alignment is performed in "order of time series", the aligning part 36 uses time indicated in the time stamp of the area cursor 81 as time of setting of the result label 82. The aforementioned "order of disposition" means that when scanning is performed along one direction on the display, for example, from the top to the bottom, or from left to right, the alignment is performed in ascending order or descending order of the values of the x-coordinate or y-coordinate of the result label 82 attached to the area cursor 81. In this embodiment, as the coordinate of the result label 82, the coordinate of the end point of the area cursor 81 is used.

The aligned result labels are displayed so that the separated labels are displayed in the order of the alignment, or so that the separated labels are collectively displayed in one frame. Such a frame in which a plurality of labels is collectively displayed will be henceforth referred to as label box. FIG. 6 (*a*) shows an example of the former case, and shows a state that three of the separated result labels 82-1, 82-2, and 82-3 aligned in the "order of disposition" for the initial y-coordinate are individually displayed. FIG. 6 (*b*) shows an example of the latter case, in which three of the separated result labels 82-1, 82-2, and 82-3 are accommodated in one label box 84, aligned in the "order of the identification name", and displayed. Degradation of the visibility of the separated result labels 82-1, 82-2, and 82-3 due to undue separation of the labels can be thereby prevented.

When an arbitrary result label is chosen from those included in the label box 84, the label box can be divided into a divided label box including the selected result label and result label or labels existing under the selected result label, and a divided label box including result label or labels existing above the selected result label. That is, the label box 84 can be divided at the position of the selected result label.

For example, FIG. 7 (*a*) shows a state that the result label 82-1 is chosen and moved. In this case, all of the result label 82 and the result labels existing under the result label 82 (corresponding to the whole result label box 84 in this example) can be moved together.

FIG. 7 (*b*) shows a state that the result label 82-2 is chosen and moved. In this case, the label box 84 is divided into a divided label box 84*b* including the result label 82-2 and the result label existing under the result label 82-2, and a divided label box 84*a* including the result label existing above the result label 82-2 (label box including only the result label 82-1), and only the divided label box 84*b* can be moved. Processing for generation, display, and division of the label box 84 mentioned above is performed by the cursor processing part 34. Since the result labels 82-1, 82-2, and 82-3 are accommodated in the label box 84, they can be visually recognize together, and the desired labels can be moved together, thus resulting easier operation. For example, for a branching blood vessel, result labels set for the branches can be displayed together, and result labels and label box desired by the operator can be displayed.

As for the display position of the aligned result labels 82-1, 82-2, and 82-3, or the label box 84, they may be displayed in a predetermined region in the display. For example, it may be determined beforehand that they are displayed in an upper left region of the display. The aligned result labels 82-1, 82-2, and 82-3 or the label box 84 may be displayed in a region of a medical image in which the subject is not imaged (henceforth referred to as "non-subject region"), so that the aligned result labels or the label box obstructs diagnosis. Examples of the non-subject region are shown in FIG. 8. The non-subject region is a non-field-of-view region 101 in an ultrasonogram 100 except for the field-of-view region 103 in the case of the ultrasonogram 100 (refer to FIG. 8 (*a*)), an air region 111 existing around the subject region 113, in which only air is imaged, in the case of an X-ray CT image 110 (refer to FIG. 8 (*b*)), or an X-ray shutter region 121 in which X-ray shutter is imaged or a direct X-ray exposure region 122 existing around a subject region 123, which directly receives irradiation of X-ray, in the case of an X-ray image 120 (refer to FIG. 8 (*c*)). Detection of such non-subject regions as mentioned above may be based on calculation performed by a region detection part 37 using pixel values (density values) of the medical image. The X-ray shutter region 121 may be detected by providing a position detection part for detecting the position of the X-ray shutter, such as encoder, in an X-ray imaging apparatus, and performing calculation of coordinates of the X-ray shutter region in a medical image with the region detection part 37 on the basis of signals outputted by the encoder to detect the X-ray shutter region 121. Although FIGS. 8 (*a*), 8 (*b*), and 8 (*c*) show examples in which the label box 84 is displayed in the non-subject region, aligned result labels may be displayed instead of the label box 84.

When a non-subject region is detected, the cursor processing part 34 obtains coordinates of the non-subject region on a medical image from the non-subject region detection part 37, and converts the coordinates into coordinates in the display. Then, aligned result labels are displayed in the non-subject region of the display.

According to this embodiment, visibility of peripheral parts of the measurement area can be improved by displaying the result labels at a position separated from the measurement area. Further, if the result label is separated, the identification label is displayed in a state of being fixed to the area cursor indicating measurement result, therefore correlation of the identification information in the identification label and the identification information in the result label becomes clear, and it becomes easy to understand the measurement result of the area cursor of which part the result value of the result label indicates.

Furthermore, since the separated result labels can be aligned and displayed according to a predetermined rule, visibility of the result labels is improved. Further, when the result labels are aligned and displayed, by displaying them in a non-subject region, such a problem that the displayed result labels overlap with a diagnosis region to degrade usefulness of medical image for diagnosis can be avoided.

The aforementioned embodiment has been explained for an area cursor in the form of line segment as an example. However, when the measurement area is defined with an angle or area, an area cursor consisting of a plurality of line segments indicating a measurement angle, or an area cursor in the form of a plane indicating a measurement area may also be used. Also in such a case, the result label can be displayed in a state that it is attached at the end point of the inputted area cursor, and the same operations as those mentioned above can be performed. For example, as shown in FIG. 9 (*a*), in a medical image 130 obtained by capturing an image of the spine 131 of a subject, area cursor 81α and area cursor 81β for measuring angle of the spine 131 may be set, open angle between the area cursor 81α and area cursor 81β may be measured as the measurement object, and the measurement result may be included in a result label 82α and displayed. FIG. 9 (*a*) shows a state that the result label 82α is separated from the end point of the area cursor 81β, and identification labels 83α and 83β are displayed at the end points of the area cursors 81α and 81β. When a peak is formed by positioning one end points of the area cursors 81α and 81β at the same position as in the case of angle measurement, the identification label and the result label may be attached to free ends of the area cursors in the form of line segment instead of end points. Further, although the above example has been explained by describing that end points are positioned at the same position, angle measurement can of course be performed for an angle formed at an intersection point of a plurality of area cursors, either.

Further, as shown in FIG. 9 (b), on a visible image 140, which is an image of a member 141 of a subject, for example, an arm, a result label 82γ may be attached to an area cursor 81γ for measuring area of a wounded part 142 such as burned part, and displayed. In the case of the area cursor for measuring area, the measurement area is defined as a closed region, the starting point and the end point are the same. Therefore, the cursor processing part 34 may attach the result label 82γ or the identification label (not shown in the drawing) at the position of the starting point and end point, and displayed. Further, a three-dimensional measurement area may be set in a three-dimensional image, and volume of the measurement area may be measured and displayed.

Second Embodiment

This embodiment is characterized in that, in addition to the basic operations of the cursor processing part 34, namely, when the operation part 50 (first operation part) receives specification of a measurement area, the cursor processing part 34 displays an area cursor, and when the measurement performed by the measurement part is completed, the cursor processing part 34 attaches a result label to one end point of the area cursor and displays them, the cursor processing part 34 further displays an end point cursor that indicates an end point of the measurement area.

As explained for the first embodiment, when a measurement area is set by using an area cursor, positions of end points (starting point and end point) are inputted. However, unless these can be correctly inputted, the measurement area cannot be correctly specified. Therefore, in order to clarify the end points of the area cursor, an end point cursor for clearly indicating an end point is used together with the area cursor. In this case, the operation part 50 (first operation part) may specify the measurement area through an operation of moving the end point cursor.

The operation part (first operation part) 50 can receive an operation of specifying positions of the starting point and end point of the measurement area. In this case, when the first operation part receives an operation of specifying the position of the starting point of the measurement area, the cursor processing part 34 may display an end point cursor at the starting point position, and may not display the end point cursor that has been displayed at the starting point position, but displays an area cursor indicating a region from the starting point position to the end point position, while the first operation part receives an operation of specifying a region from the starting point position to the end point position, and when the first operation part receives an operation of specifying the end point of the measurement area, the cursor processing part 34 may display two end point cursors indicating the both respective end points of the area cursor.

The end point cursor may comprise, for example, a planer region part, which serves as a direction point when a moving operation is performed through the first operation part, and a projection part projecting from the planer region. In this case, the cursor processing part 34 displays the area cursor in the form of line segment and two end point cursors attached to the both end points of the area cursor, the end point cursors are attached to the area cursor at the projection part, and the planer region part of each end point cursor may be disposed at a position opposite to the area cursor with respect to the projection part, so that the center line of the planer region part locates on the same straight line as the area cursor.

Further, the cursor processing part 34 may display the area cursor in the form line segment of which both ends have an arrow shape, and display the end point cursors disposed around the both end points of the area cursor separately from the end points.

Further, in this embodiment, mode can be switched between a settled mode after completion of the measurement of the measurement area (display mode for displaying the result label attached to the area cursor), and an edition mode for changing the measurement area (display mode for displaying the area cursor and the end point cursor) by using the first operation part, and the end point cursor can be displayed or undisplayed in a manner corresponding to this switching of the mode.

Figure 10:
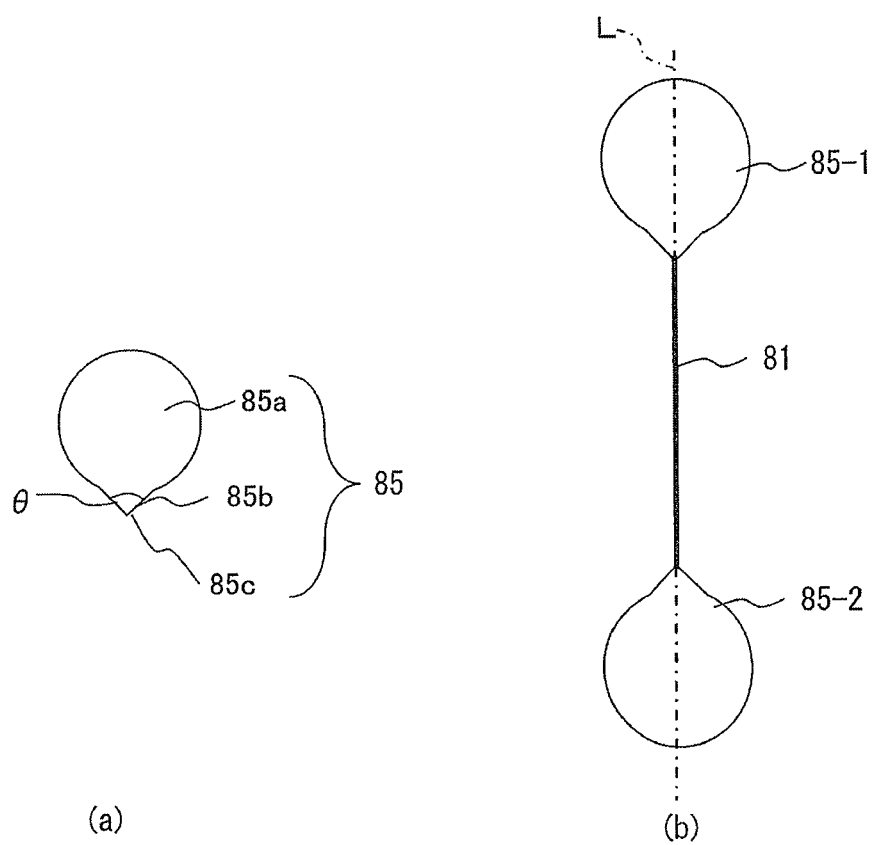
FIG. 10 is an explanatory drawing for explaining configuration of the area cursor attached with an end point cursor, in which (a) is an example of the end point cursor and (b) is an area cursor attached with end point cursors at both end points thereof.

Hereafter, this embodiment will be explained in detail with reference to FIGS. 10 to 13. The configuration of the end point cursor will be explained first with reference to FIG. 10. FIG. 10 includes explanatory drawings showing configurations of the area cursor attached with the end point cursors. FIG. 10 (a) shows an example of the end point cursor, and FIG. 10 (b) shows an area cursor to which end point cursors are attached at both end points thereof.

As shown in FIG. 10 (a), the end point cursor 85 includes a planer region part 85a that indicates a region to which a direction for changing the position of the end point cursor 85 is given, and a projection part 85b projecting outward, seeing from the center of the planer region part 85a, to the outside of the planer region part 85a. The end point cursor 85 is attached to the area cursor 81 at a tip part 85c of the projection part 85b. The planer region part 85a may have any geometrical shape. Further, a smaller internal angle θ of the tip part 85c of the projection part 85b can provide a smaller area of peripheral parts of the end of the measurement area covered by the planer region part 85a, and makes it easier to secure visually recognizable area of the measurement area.

When the end point cursors are attached to the both end points of the area cursor 81, they are disposed so that the center line L of two of the end point cursors 85-1 and 85-2, and the axis of the area cursor 81 are locate on one straight line, and the end point cursors 85-1 and 85-2 locate on the opposite sides of the area cursor 81 with respect to the attaching points of the end point cursors 85-1 and 85-2 and the area cursor 81, respectively, as shown in FIG. 10 (b). Since the area cursor 81 is set in the subject region including an object of the measurement (for example, blood vessel), by disposing the end point cursors 85-1 and 85-2 as described above, area where the end point cursors 85-1 and 85-2 overlap with the measurement object can be minimized.

Figure 11:
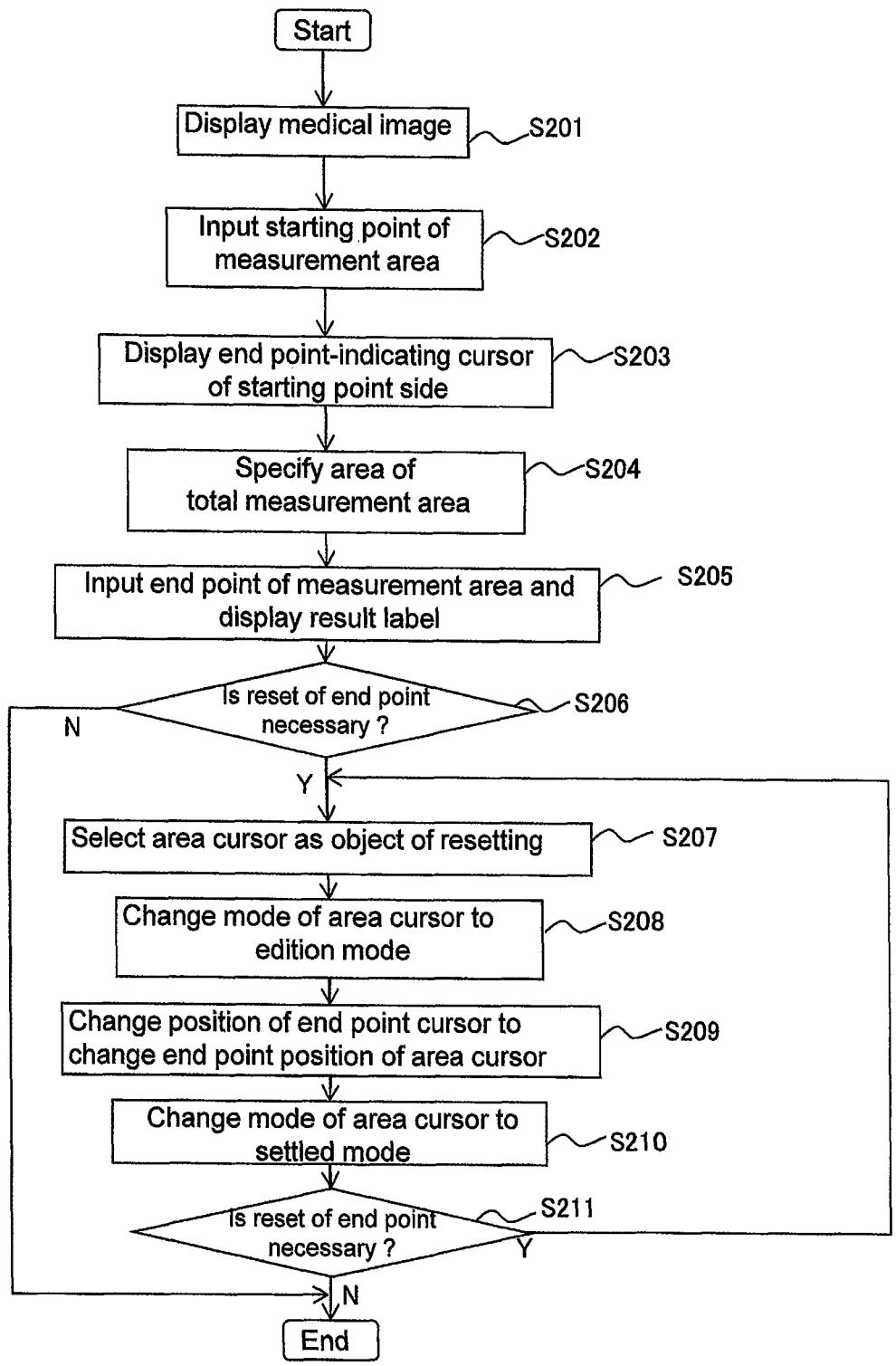
FIG. 11 is a flowchart showing flow of processing for input and edition of the area cursor using the end point cursor.
Figure 12:
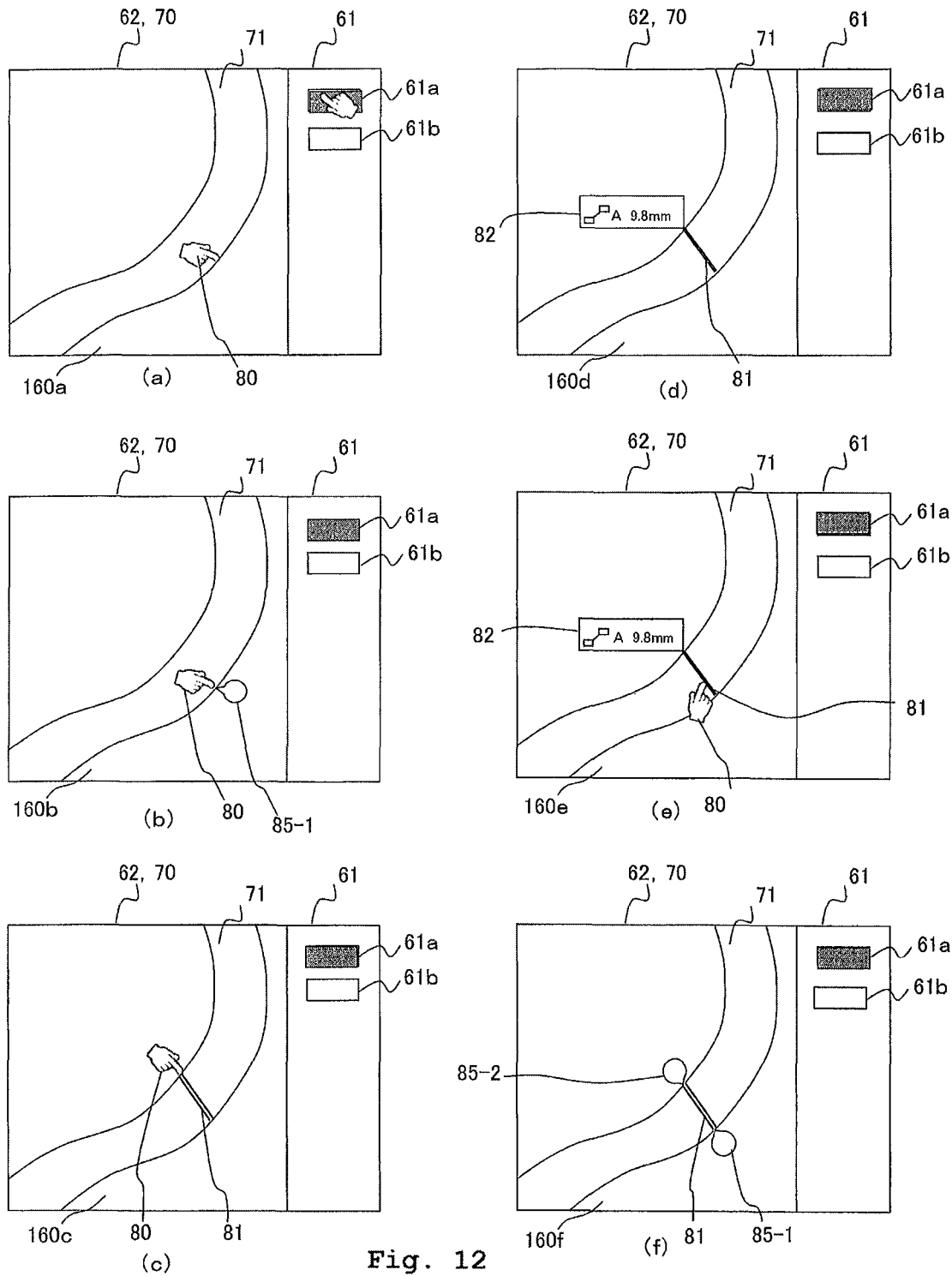
FIG. 12 is an explanatory drawing showing an example of transition of display displayed along the flow of the processing for input and edition of the area cursor using the end point cursor, in which (a) is an example of display displayed in Step S201, (b) is an example of display displayed in Step S203, (c) is an example of display displayed in Step S204, (d) is an example of display displayed in Step S205, (e) is an example of display displayed in Step S207 and (f) is an example of display displayed in Step S208.

Hereafter, the processing for setting the area cursor by using the end point cursor, and finely adjusting the position of the end point of the set area cursor will be explained with reference to FIGS. 11 to 13. FIG. 11 is a flowchart showing the flow of processing for input and edition of the area cursor using the end point cursor. FIG. 12 includes explanatory drawings showing examples of transition of display corresponding to the flow of the processing for input and edition of the area cursor using the end point cursor. In FIG. 12 (a) shows an example of display displayed in Step S201, (b) shows an example of display displayed in Step S203, (c) shows an example of display displayed in Step S204, (d) shows an example of display displayed in Step S205, (e) shows an example of display displayed in Step S207, and (f) shows an example of display displayed in Step S208. FIG. 13 includes explanatory drawings showing a processing for changing position of the end point of the area cursor by using the end point cursor, where (a) shows a state before the change, and (b) shows a state after the change. In the following explanation, the mode in which the area cursor 81 attached with the end point cursor 85 is displayed is referred to as "edition mode", and the mode in which the area cursor 81 attached with the result label 82 or the identification label 83 is displayed is referred to as "settled mode". Hereafter, explanations will be made in the order of the steps shown in FIG. 11.

Before the start of the measurement processing shown in FIG. 11, an image of a subject is captured with the image-capturing part 10, and image signals are obtained. The image generation part 31 generates a medical image on the basis of the image signals, and stores it in the image storage part 32. The following steps are started after a medical image is generated as described above.

(Step S201)

The image selection and display control part 33 reads out a medical image as an object of the measurement, and displays it on the screen of the display part 40 (S201). A display 160*a* shown in FIG. 12 (*a*) is an example of display on the screen at the end of this step. The display 160*a* includes a button region 61 where software buttons are displayed, and an image display region 62 where a medical image is displayed. In the display 160*a*, a medical image 70 in which a blood vessel 71 is captured is displayed in the image display region 62. In the button region 61, there is displayed the "Measurement" button 61*a* for inputting a direction for starting the measurement.

(Step S202)

The starting point of the measurement area is inputted (S202). Hereafter, explanations will be made for a processing of measuring width of the blood vessel 71 as an example. The operator operates the operation part 50 to move the mouse cursor 80 to the starting point of the measurement area, i.e., one end part of the width of the blood vessel 71 as the object of the measurement, and performs an operation for inputting the position (for example, clicking a mouse button) (S202).

(Step S203)

The cursor processing part 34 superimposingly displays the end point cursor 85-1 on the medical image 70 so that the tip of the end point cursor 85-1 locates at the position of the tip of the mouse cursor 80 as displayed in the display 160*b* shown in FIG. 12 (*b*) (S203). The end point cursor 85-1 is displayed in an initially set direction. In the display 160*b*, the end point cursor 85-1 is displayed in such a direction that the centerline thereof is parallel to the horizontal direction of the display.

(Step S204)

The area of the whole measurement area is specified (S204). When the operator starts to move the mouse cursor 80 using the operation part 50, the cursor processing part 34 changes the display so that the end point cursor 85-1 is not displayed, and displays tracing of the movement of the mouse cursor 80 with a line segment of which one end is the starting point. The cursor processing part 34 uses this line segment to generate and display the area cursor 81. The operator performs operation of moving the mouse cursor 80 to the end point of the measurement area. The display 160*c* shown in FIG. 12 (*c*) is an example of display displayed at the end of this step.

(Step S205)

When the end point of the measurement area is inputted, measurement for the measurement area is performed, and a result label is displayed (S205). According to this embodiment, if the operator moves the mouse cursor 80 to the end point and performs an operation for inputting the end point position (for example, clicking a mouse button), the measurement part 38 measures the length of the line segment specified by the area cursor 81. Then, the cursor processing part 34 generates the result label 82 including the result value of the aforementioned length measurement, attaches it to the end point of the area cursor 81, and displays them. The display 160*d* shown in FIG. 12 (*d*) is an example of the display displayed at the end of this step. In this display 160*d*, the area cursor 81 is displayed in a state of being attached with the result label 82, i.e., in the settled mode, but in this settled mode, edition operation such as resetting of the starting point and end point positions of the area cursor 81 cannot be performed.

(Step S206)

If the starting point and end point of the area cursor 81 deviate from the positions of the ends of the object of the measurement, correct measurement result cannot be obtained. In such a case, it becomes necessary to reset the position of the starting point or end point of the area cursor 81. Therefore, the operator judges whether resetting of the starting point or end point position of the area cursor 81 is necessary or not, and advances the processing to Step S207, if necessary, or ends the processing, if unnecessary.

(Step S207)

The area cursor for performing resetting of the measurement area is selected (S207). This selection can be performed by, for example, moving the mouse cursor 80 to the area cursor 81 as the object of the resetting of the measurement area, as shown in display 160*e* shown in FIG. 12 (*e*), and performing a selection operation (for example, clicking a mouse button). This selection performed with the mouse is switching of the display and is also switching of the function.

(Step S208)

The cursor processing part 34 switches the display of the area cursor 81 of the settled mode to that of the edition mode. That is, the result label 82 is made undisplayed, and the area cursor 81 attached with the end point cursors 85-1 and 85-2 at the both ends thereof is displayed (S208). In the display 160*f* shown in FIG. 12 (*f*), the area cursor 81 changed into that of the edition mode is displayed.

(Step S209)

In the edition mode in which the end point cursors are displayed, the operator changes the position of the end point cursor 85-1 or 85-2 to change the position of the end point of the area cursor 81 (S209). The processing of this step is explained with reference to FIG. 13.

For example, in FIG. 13 (*a*), the tip of the end point cursor 85-2 locates on a profile line 71*a* of the blood vessel 71, but the tip of the end point cursor 85-1 locates in a cavity region 71*b* in the blood vessel 71. Therefore, the length of the area cursor 81 is shorter than the diameter of the blood vessel 71, and a value smaller than the actual vessel diameter will be measured.

Therefore, the operator moves the mouse cursor 80 to the planer region part 85*a*-1 of the end point cursor 85-1, and drags it so that the tip of the end point cursor 85-1 locates on the profile line 71*a* of the blood vessel 71.

FIG. 13 (*b*) shows an example of the display on the screen after the end point cursor 85-1 has been moved. In the display shown in FIG. 13 (*b*), both the end point cursors 85-1 and 85-2 locate on the profile lines 71*a* of the blood vessel 71, and the length of the area cursor 81 is the same as the vessel diameter of the blood vessel 71. Therefore, the vessel diameter can be correctly measured. The mode using the area cursor for specifying the end point of the measurement area from the outside of the object of the measurement as shown in FIG. 13 is referred to as "outside measurement mode".

Following the position change of the end point cursor 85-1, the cursor processing part 34 changes the directions of the end point cursors 85-1 and 85-2, so that the centerlines of the planer region parts 85a-1 of 85-2 of the end point cursor 85-1 and 85a-2 and the area cursor 81 locate on one straight line.

(Steps S210 and S211)

The display mode of the area cursor is changed to the settled mode from the edition mode (S210). The operator performs a mode switching operation by using the operation part 50 (for example, clicking a part of the area cursor 81 of the edition mode with a mouse). The cursor processing part 34 makes the end point cursor 85 undisplayed, and the measurement part 38 measures a physical quantity of a newly set area cursor 81. The cursor processing part 34 generates a result label 82 including the result of the measurement, and displays it. When it is necessary to change the mode to the edition mode again (S211), the process returns to Step S206.

The switching of the mode from the edition mode to the settled mode is performed by the operator by performing a mode switching operation. Alternatively, there may also be employed a configuration that the cursor processing part 34 measures lapsed time from the time of the last operation performed for the area cursor 81 in the edition mode, and when a predetermined time defined beforehand passes, the display is automatically changed to that of the settled mode.

According to this embodiment, by using the end point cursor, the measurement area can be set with maintaining favorable visibility of the end point of the measurement area. Further, since the area cursor is inputted and edited by using the end point cursor, the position of the end point of the area cursor becomes clear, and thus the accuracy of the setting of the measurement area can be improved. In addition, also in this embodiment, the following configurations may be employed as in the first embodiment. That is, the result label 82 displayed in the settled mode (FIG. 12 (e)) may be moved to an arbitrary position as required, and the identification label may be displayed at the end point of the area cursor at which the result label 82 has been attached. Further, when the measurement is performed for a plurality of points, a plurality of appropriately aligned result labels, or result labels accommodated in a label box may be displayed. Furthermore, the label box may be constituted so that it can be arbitrarily divided.

Third Embodiment

This embodiment is characterized by the shape of the area cursor chosen according to the type of measurement mode or imaging method employed in the medical image-capturing device, and addition of an additional cursor. Examples of the measurement mode include, for example, mode for measuring the shortest distance used when diameter of vessel cavity or organ is measured (shortest distance measurement mode), mode for measuring internal diameter (inside measurement mode), mode for measuring external diameter (outside measurement mode), and so forth. Cursor shapes and novel cursors suitable for these measurement modes are created and displayed. Selection of the measurement mode can be received through the operation part.

Specifically, the cursor processing part 34 can add a guiding line to each end point of the area cursor, which guiding line is perpendicular to the axial direction of the area cursor in the form of line segment, and display them.

The cursor processing part 34 may display a popup menu for choosing a display mode in which the guiding line is added to each end point of the area cursor, or a display mode in which the guiding line is not added.

Further, the cursor processing part 34 may obtain imaging technique information from the image-capturing part 10, and display the area cursor in a shape corresponding to the imaging technique information.

Figure 14:
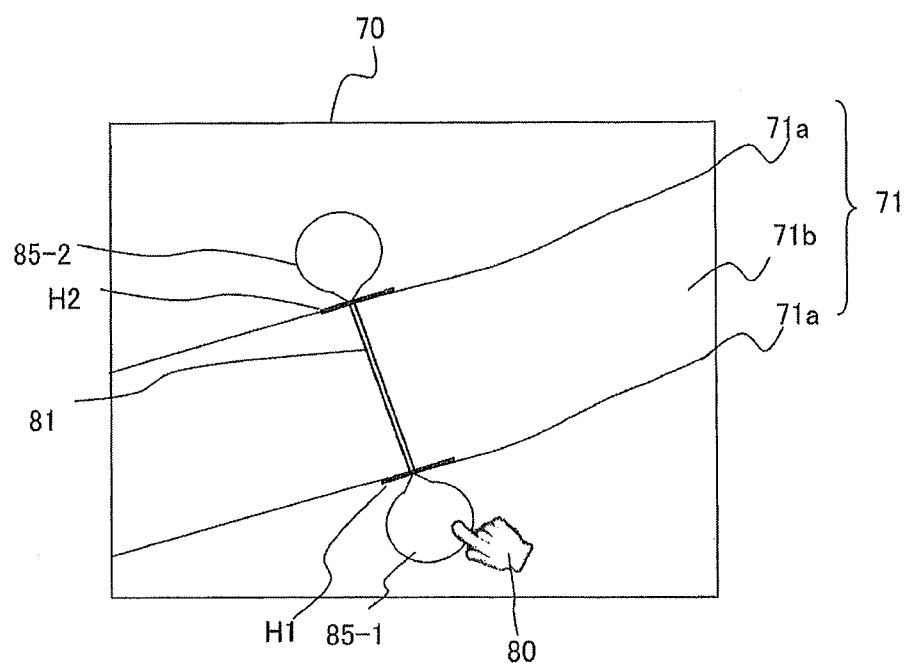
FIG. 14 is an explanatory drawing showing configuration of the area cursor used in the shortest distance measurement mode.
Figure 15:
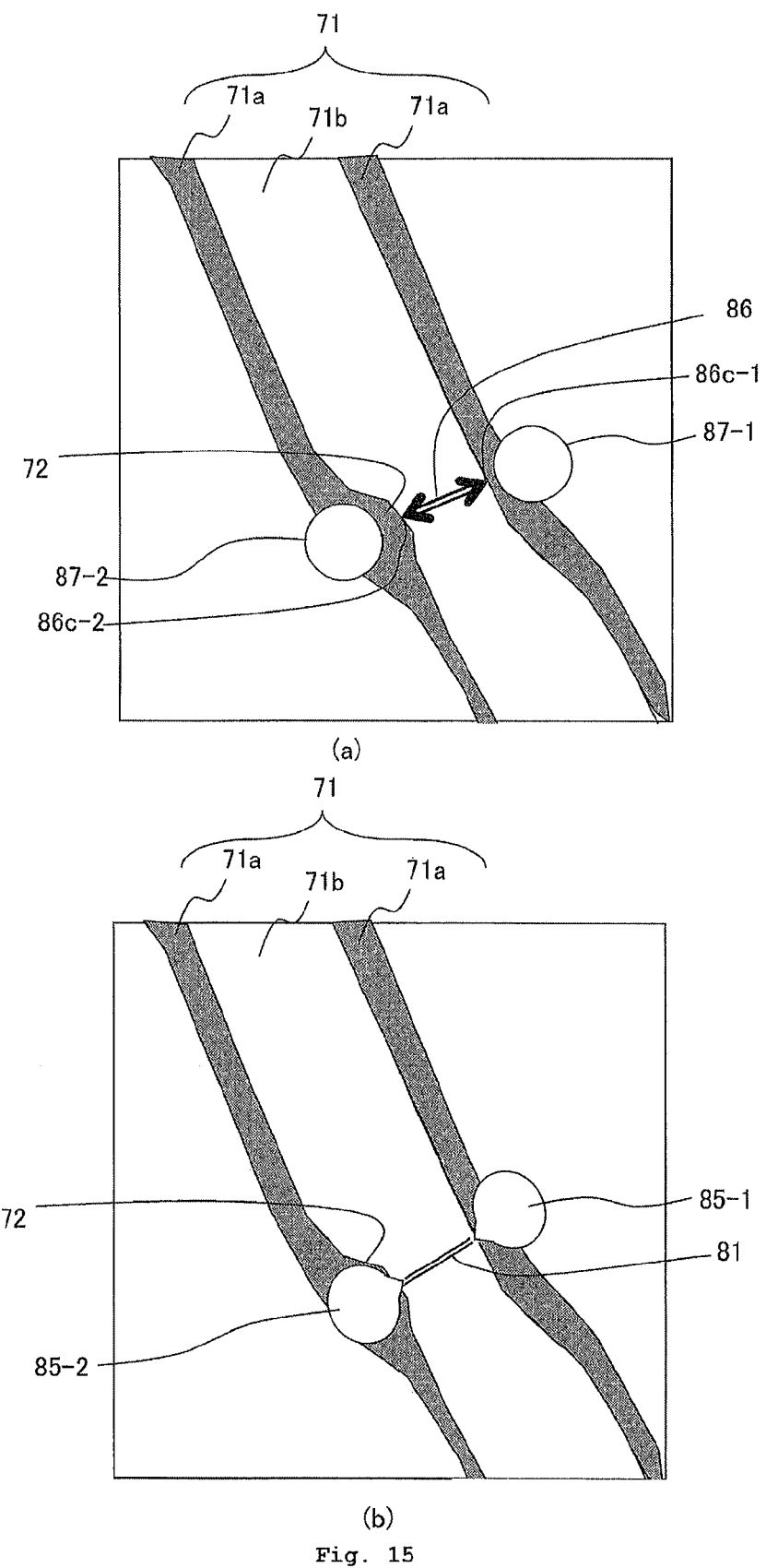
FIG. 15 is an explanatory drawing for explaining configurations of the area cursor and end point cursor used in the inside measurement mode, in which (a) is an example of the configuration of the end point cursor used in the inside measurement mode and (b) is an comparative example using area cursor and end point cursor used in the outside measurement mode.
Figure 16:
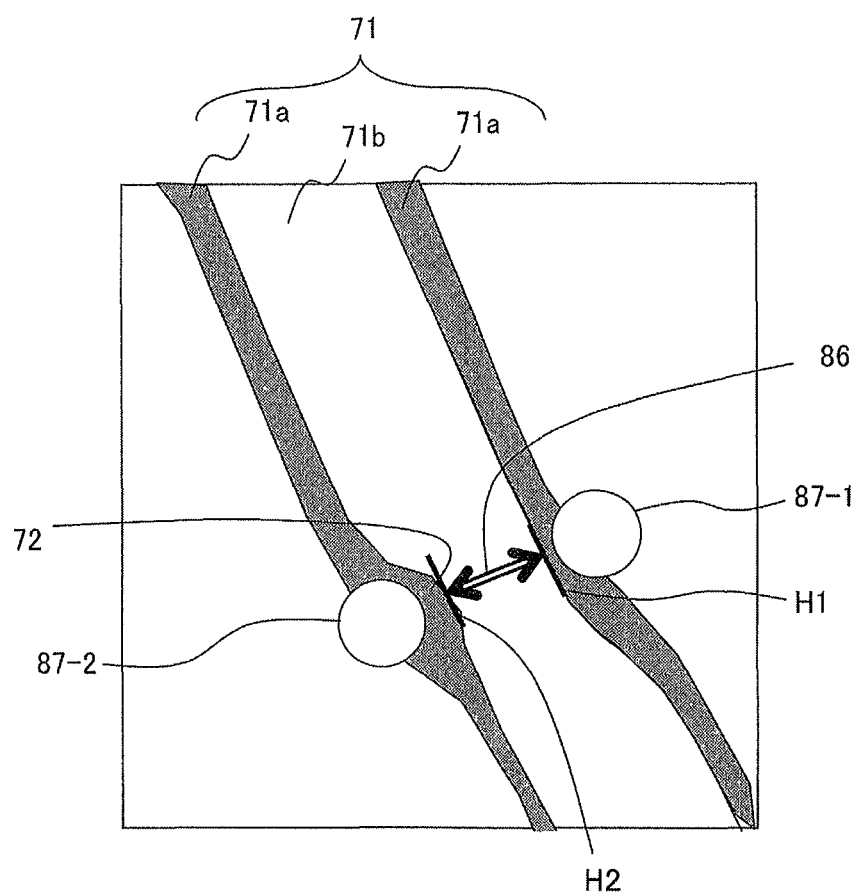
FIG. 16 is an explanatory drawing showing the area cursor used in the shortest distance measurement mode with inside measurement lines.
Figure 17:
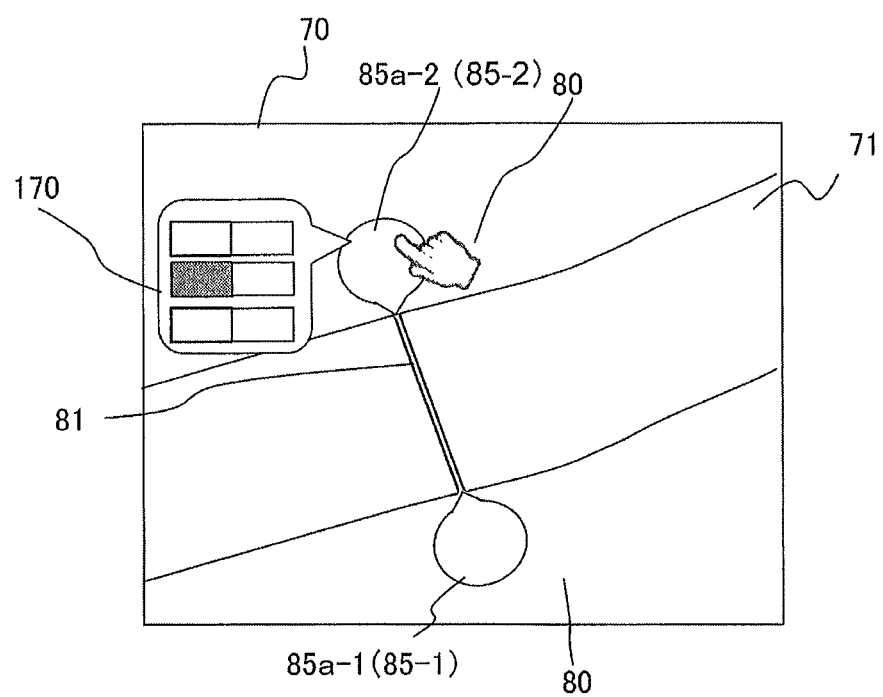
FIG. 17 is an explanatory drawing showing an example of measurement mode switching processing.

Hereafter, this embodiment will be explained in detail with reference to FIGS. 14 to 17. The processing of this embodiment is similar to those of the first and second embodiments, and the differences will be mainly explained below. FIG. 14 is an explanatory drawing showing configuration of the area cursor used in the shortest distance measurement mode. FIG. 15 includes explanatory drawings for explaining configurations of the area cursor and end point cursor used in the inside measurement mode, wherein FIG. 15 (a) shows an example of the configuration of the end point cursor in the inside measurement mode, and FIG. 15 (b) shows an comparative example using area cursor and end point cursors used in the outside measurement mode. FIG. 16 is an explanatory drawing showing the area cursor used in the shortest distance measurement mode using inside measurement lines. FIG. 17 is an explanatory drawing showing an example of measurement mode selection operation using popup display.

As shown in FIG. 14, in the shortest distance measurement mode, guiding lines H1 and H2 are added to the both end points of the area cursor 81 in the edition mode so that the guiding lines are perpendicular to the axial direction of the linear area cursor 81. When the distance is measured in the shortest distance measurement mode, by providing the guiding line H at the end of the object of the measurement, or providing the guiding lines H on the tangential lines of the profile lines 71a of the blood vessel 71 in the case shown in FIG. 14, the position on the other side of the object of the measurement (giving the shortest distance) can be correctly set.

Further, in the example shown in FIG. 14, the tips of the end point cursors 85-1 and 85-2 are moved to the end points of the area cursor 81 from the outside of the measurement object. However, end point-indicating parts may be provided on the area cursor, and the end point-indicating parts may be moved by using an end point cursor provided separately from the area cursor.

An example of the area cursor provided with the end point-indicating parts and the end point cursors for moving the end point-indicating parts is shown in FIG. 15 (a). The area cursor 86 shown in FIG. 15 (a) is constituted with an inside measurement line having arrows indicating end points of the measurement area on the both ends as the end point-indicating parts, and the end points of the area cursor 86 are specified by using tips 86c-1 and 86c-2 of the arrows. Further, end point cursors 87-1 and 87-2 are displayed separately from the area cursor 86 on extension lines of the area cursor 86 for the axial direction. By moving the mouse cursor 80 to the end point cursor 87-1 or 87-2 and dragging it, the position of the tip 86c-1 or 86c-2 of the arrow of the area cursor 86 locating at a position relatively nearer to the end point cursor 87-1 or 87-2 is changed.

The line for inside measurement (line segment of the area cursor) is effective when it is more desirable to specify the end points of the measurement area from the inside of the measurement object part. For example, when diameter of a cavity region 71b of a blood vessel is measured at a position where a soft plaque 72 adheres to the intravascular wall 71a of the blood vessel, if the end points are specified from the outside of the cavity region 71b, the end point cursor 85-1 or 85-2 overlaps with the soft plaque 72 as shown in FIG. 15 (b), and thus it becomes difficult to visually recognize where the part of the largest thickness of the soft plaque 72 is (namely, the part where the blood vessel is most constricted). In such a case, by using the inside measurement line in combination with end point-indicating parts such as arrows, the measurement area can be specified from the inside of the cavity region 71b with visually recognizing the shape of the soft plaque 72, and an area cursor suitable for inside measurement can be constituted. Further, as shown in FIG. 16, the perpendicular guiding lines H1 and H2 may be added to the area cursor 86 using the aforementioned line for inside measurement, so that the inside measurement can be performed also in the shortest distance measurement mode. In the case of the outside measurement mode for measuring external diameter of a vessel or the like, the measurement can be performed with such an area cursor 81 as shown in FIG. 10 or FIG. 13.

The aforementioned switching of the mode among the shortest distance measurement mode, inside measurement mode, and outside measurement mode will be explained with reference to FIG. 17. FIG. 17 is an explanatory drawing showing an example of the measurement mode switching processing. If the operator clicks the planer region part 85a-1 or 85a-2 of the end point cursor 85-1 or 85-2 for a long time with the mouse cursor 80, the cursor processing part 34 displays a popup menu 170 for selecting the mode, which pops up from the planer region part 85a-1 or 85a-2. If the operator performs an operation for selecting any one of the modes, the cursor processing part 34 displays the area cursor of the selected mode. For example, when the shortest distance measurement mode is selected, the area cursor to which the perpendicular guiding lines are added is displayed, or when the inside measurement mode is selected, the area cursor to which the end point-indicating parts are added is displayed. Further, it may also be configured so that whether the guiding lines are displayed or not can be selected on the popup menu.

Further, the measurement mode may be switched according to the imaging type employed in a medical image-capturing device. Specifically, there may be employed a configuration that when an imaging method (imaging type) is chosen in the image-capturing part 10, the cursor processing part 34 refers to the imaging method information of the imaging method, and displays the area cursor suitable for the selected imaging method. For example, for the DSA imaging (digital subtraction angiography), there may be employed a configuration that the area cursor for the shortest distance measurement mode is initially displayed for measurement of blood vessel diameter. With such a configuration as described above, an area cursor suitable for the shape of the measurement object part can be displayed.

According to this embodiment, the end point cursor and area cursor suitable for the characteristics of the measurement object part, such as those for the outside measurement mode, inside measurement mode, shortest distance measurement mode, etc. can be provided, and by using them, the measurement area can be appropriately set. Further, by using a popup menu for display for the selection of the mode, the selection menu can be displayed only when the mode selection is required, and the selection menu can be undisplayed after the mode selection is completed. Thus, a wider display region of a medical image can be thereby secured, and visibility can be improved.

Fourth Embodiment

According to this embodiment, to the image display device of the embodiment in which the mode can be switched between the settled mode (display mode for displaying the area cursor attached with the result label) and the edition mode (display mode in which the area cursor and the end point cursor are displayed) (second embodiment), a function of setting a region on the area cursor around the end point of the area cursor as a selection-forbidden region of which selection as an object of the aforementioned mode switching operation is forbidden is added.

Figure 18:
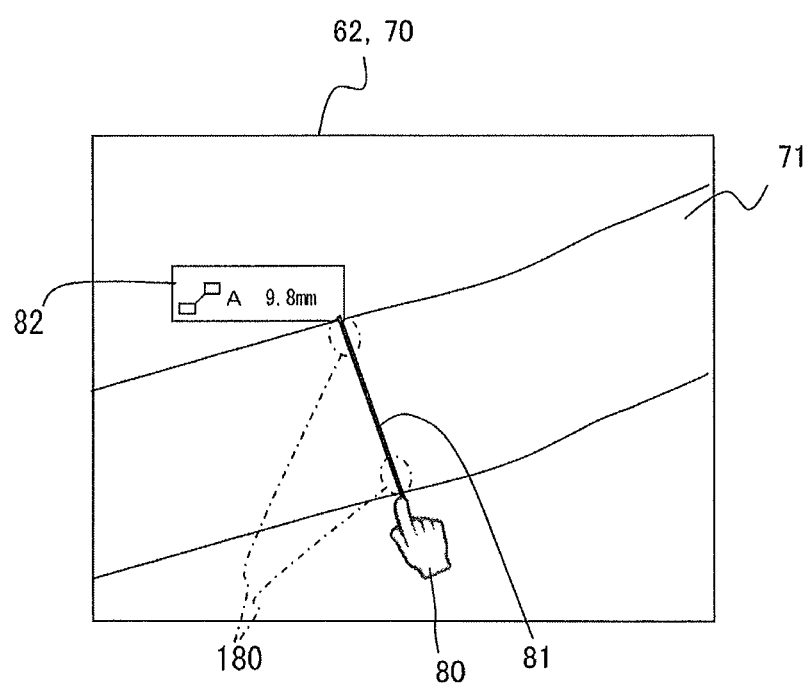
FIG. 18 is an explanatory drawing showing a selection-forbidden region.

In the second embodiment, switching of the mode from the settled mode to the edition mode is performed by, for example, moving the mouse cursor to the area cursor and clicking a mouse button. However, in this embodiment, the cursor processing part 34 sets a selection-forbidden region in a predetermined region around each end point of the area cursor 81. Even if the mouse cursor 80 is moved to this selection-forbidden region and the clicking operation is performed, selection of that area cursor 81 is not received, but the position selected with the mouse cursor 80 is set as a starting point of a new area cursor 81. The selection-forbidden region is explained with reference to FIG. 18. FIG. 18 is an explanatory drawing showing a selection-forbidden region.

For example, in the case of measurement of angle (refer to FIG. 9 (a)), end points of a plurality of area cursors 81 may come close to each other, or overlap with each other. In the second embodiment, the area cursor 81 is selected, and then the switching operation for switching the mode to the edition mode or settled mode is performed. However, if the total regions of the area cursors 81 are selection-receivable regions, fault may occur in the operation for selecting closely locating area cursors 81. That is, if it is attempted to set a starting point of a new area cursor for measuring an angle, the mode is switched, and a new area cursor cannot be set. Therefore, a predetermined region around the end point of the area cursor 81 is set as a selection-forbidden region 180, and it is determined that the operation for selecting the area cursor 81 is not received in this region. If an operation of clicking a mouse button or the like is received within the selection-forbidden region 180, the cursor processing part 34 recognizes the operation as an operation for setting a new area cursor, and starts a processing for inputting the starting point. This makes it possible to avoid unnecessary operation errors. Further, the aforementioned selection-forbidden region can also be used for measurement other than measurement of angle.

According to this embodiment, by providing the selection-forbidden region in the vicinity of the end point of the area cursor, the mode selection operation and new area cursor setting operation can be smoothly performed.

DESCRIPTION OF NUMERICAL NOTATIONS

1: Medical image-capturing device, 10: image-capturing part, 20: image display device, 30: control part, 31: image generation part, 34: cursor processing part, 35: cursor information storage part, 36: aligning part, 37: non-subject region detection part, 38: measurement part, 40: display part, 50: operation part (first operation part and second operation part)

The invention claimed is:

1. An image display device comprising:
a first operation part that receives an operation of specifying a measurement area on a medical image displayed on a screen of a display device,
a measurement part that measures a physical quantity of the measurement area,
a cursor processing part that performs control for generating an area cursor that indicates the measurement area, an identification label including identification information for specifically identifying the area cursor, and a result label including the identification information and a measurement result obtained by the measurement part, and displaying them on the screen, and
a second operation part that receives an operation of moving the result label,
wherein:
when the first operation part receives specification of the measurement area, the cursor processing part displays the area cursor, when the measurement performed by the measurement part is completed, the cursor processing part attaches the result label to one end point of the area cursor and displays them, and when the second operation part receives an operation of moving the result label, the cursor processing part separates the result label from the area cursor and displays it following the moving operation, and displays the identification label at the one end point of the area cursor at which the result label has been attached.

2. The image display device according to claim 1, wherein:
the cursor processing part further displays an end point cursor that indicates an end point of the measurement area, and
the first operation part specifies the measurement area through an operation of moving the end point cursor.

3. The image display device according to claim 2, wherein:
the first operation part receives an operation of specifying positions of starting point and end point of the measurement area,
when the first operation part receives the operation of specifying position of starting point of the measurement area, the cursor processing part displays the end point cursor at the starting point position,
the cursor processing part does not display the end point cursor that has been displayed at the starting point position, but displays an area cursor indicating a region from the starting point position to the end point position, while the first operation part receives an operation of specifying a region from the starting point position to the end point position, and
when the first operation part receives an operation of specifying the end point of the measurement area, the cursor processing part displays two end point cursors indicating the both end points of the area cursor, respectively.

4. The image display device according to claim 3, wherein:
the end point cursor comprises a planer region part, which serve as a direction point when a moving operation is performed through the first operation part, and a projection part projecting from the planer region,
the cursor processing part displays the area cursor in the form of line segment and two of the end point cursors attached to the both ends point of the area cursor, the end point cursors are attached to the area cursor at the projection part, and the planer region part of each end point cursor is disposed at a position opposite to the area cursor with respect to the projection part, so that the center line of the planer region part locates on the same straight line as the area cursor.

5. The image display device according to claim 3, wherein:
the cursor processing part displays the area cursor in the form line segment of which both ends have an arrow shape, and the end point cursors disposed around the both end points of the area cursor separately from the end points.

6. The image display device according to claim 4, wherein:
the cursor processing part adds a guiding line to each end point of the area cursor in the form of line segment, which guiding line is perpendicular to the axial direction of the area cursor, and display them.

7. The image display device according to claim 2, wherein:
the first operation part further receives an operation for switching between a settled mode in which the result label is attached to the area cursor and an edition mode in which the area cursor and the end point cursor are displayed, and
the cursor processing part sets a region on the area cursor in a predetermined region around the end point of the area cursor as a selection-forbidden region of which selection as an object of the switching operation is forbidden.

8. The image display device according to claim 1, wherein:
the image display device further comprises an aligning part that aligns result labels separated from the area cursor in accordance with a predetermined alignment condition, and
the cursor processing part displays the aligned result labels.

9. The image display device according to claim 8, wherein:
the cursor processing part generates a label box accommodating a plurality of the aligned result labels,
when the second operation part receives an operation of selecting and moving an arbitrary result label in the label box, the cursor processing part divides the label box into a plurality of divided label box at the selected result label as a border, moves a divided label box including the selected result label and displays it following the moving operation.

10. The image display device according to claim 8, wherein:
the image display device further comprises a non-subject region detection part that detects a non-subject region where a subject is not imaged in an medical image, and
the cursor processing part displays the aligned result labels in the non-subject region.

11. The image display device according to claim 1, wherein:
the cursor processing part changes type and shape of cursors to be displayed according to type of measurement mode.

12. The image display device according to claim 11, wherein:
the cursor processing part displays a popup menu for selecting the measurement mode at end point of the area cursor.

13. The image display device according to claim 11, wherein:

the cursor processing part selects the measurement mode according to imaging technique used for capturing the medical image.

14. An image display device comprising:

an operation part that receives an operation of specifying a measurement area on a medical image displayed on a screen of the display device, a measurement part that measures a physical quantity of the measurement area, and a cursor processing part that performs control for generating an area cursor that indicates the measurement area, and an end point cursor that indicates an end point of the measurement area, and displaying them on the screen, wherein:

the operation part receives an operation of specifying positions of a starting point and an end point of the measurement area, when the operation part receives the operation of specifying position of the starting point of the measurement area, the cursor processing part displays the end point cursor at the position of the starting point, the cursor processing part does not display the end point cursor that has been displayed at the starting point position, but displays an area cursor indicating a region from the starting point position to the end point position, while the first operation part receives an operation of specifying a region from the starting point position to the end point position, and when the operation part receives an operation of specifying the end point of the measurement area, the cursor processing part displays two of the end point cursors indicating the both end points of the area cursor.

15. A medical image-capturing device comprising:

the image display device according to claim 1, and an image-capturing part that captures an image of a subject and obtains image signals, wherein:

the image display device further comprises an image generation part that generates a medical image in which the subject is imaged on the basis of the image signals.

16. The medical image-capturing device according to claim 15, wherein:

the cursor processing part obtains imaging technique information from the image-capturing part, and displays the area cursor of a shape suitable for the imaging technique information.

17. The image display device according to claim 5, wherein:

the cursor processing part adds a guiding line to each end point of the area cursor in the form of line segment, which guiding line is perpendicular to the axial direction of the area cursor, and display them.

* * * * *